(12) United States Patent
Gougeon et al.

(10) Patent No.: US 10,890,583 B2
(45) Date of Patent: Jan. 12, 2021

(54) **PREDICTIVE VALUE OF *CLOSTRIDIUM DIFFICILE*-SPECIFIC IMMUNE RESPONSE FOR RECURRENCE AND DISEASE OUTCOME**

(71) Applicants: INSTITUT PASTEUR, Paris (FR); UNIVERSITE PARIS-SUD, Orsay (FR); CENTRE HOSPITALIER DE VERSAILLES, Le Chesnay (FR); ASSISTANCE PUBLIQUE-HOPITAUX DE PARIS, Paris (FR)

(72) Inventors: Marie-Lise Gougeon, Antony (FR); Alban Le Monnier, Fontenay le Fleury (FR); Anne Collignon, Paris (FR); Michel Robert Popoff, Clamart (FR)

(73) Assignees: INSTITUT PASTEUR, Paris (FR); UNIVERSITE PARIS-SUD, Orsay (FR); CENTRE HOSPITALIER DE VERSAILLES, Le Chesnay (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 40 days.

(21) Appl. No.: 15/300,309

(22) PCT Filed: Apr. 1, 2015

(86) PCT No.: PCT/EP2015/057259
§ 371 (c)(1),
(2) Date: Jul. 20, 2017

(87) PCT Pub. No.: WO2015/150493
PCT Pub. Date: Oct. 8, 2015

(65) Prior Publication Data
US 2017/0212113 A1    Jul. 27, 2017

Related U.S. Application Data

(60) Provisional application No. 61/973,508, filed on Apr. 1, 2014.

(51) Int. Cl.
*G01N 33/569* (2006.01)
*A61K 39/08* (2006.01)
*G01N 33/564* (2006.01)

(52) U.S. Cl.
CPC ........ *G01N 33/56911* (2013.01); *A61K 39/08* (2013.01); *G01N 33/564* (2013.01);
(Continued)

(58) Field of Classification Search
CPC ............... A61K 39/08; G01N 2469/10; G01N 2469/20; G01N 2800/50; G01N 2333/33;
(Continued)

(56) References Cited

U.S. PATENT DOCUMENTS

| 2011/0183360 A1* | 7/2011 | Rajagopal .......... C07K 16/1282 435/7.32 |
| 2012/0121607 A1* | 5/2012 | Shone ................ C07K 16/1282 424/167.1 |

FOREIGN PATENT DOCUMENTS

WO    2013/049214 A1    4/2013

OTHER PUBLICATIONS

Pechine et al., 2005 (journal of medical microbiology. vol. 54, No. 2, pp. 193-196. (Year: 2005).*
(Continued)

*Primary Examiner* — Jana A Hines
(74) *Attorney, Agent, or Firm* — Arrigo, Lee, Guttman & Mouta-Bellum LLP

(57) ABSTRACT

The present invention relates to the field of *Clostridium difficile* infections. Methods of diagnosing, treating and
(Continued)

preventing *Clostridium difficile*-associated disease and recurrent CDAD are disclosed herein.

6 Claims, 18 Drawing Sheets

(52) U.S. Cl.
CPC ... *G01N 33/56916* (2013.01); *G01N 2333/33* (2013.01); *G01N 2469/10* (2013.01); *G01N 2469/20* (2013.01); *G01N 2800/50* (2013.01)

(58) Field of Classification Search
CPC ........... G01N 33/564; G01N 33/56911; G01N 33/56916
See application file for complete search history.

(56) References Cited

OTHER PUBLICATIONS

Pechine et al., 2005 (Journal of Medical Microbiology. vol. 54, No. 2. pp. 193-196) in (Year: 2005).*
Xie et al., (Clinical and Vaccine Immunology Apr. 2013. vol. 20, No. 4. p. 517-525, published online Feb. 6, 2013). (Year: 2013).*
Valiente E, Dawson LF, Cairns MD, Stabler RA, Wren BW: Emergence of new PCR ribotypes from the hypervirulent Clostridium difficile 027 lineage. J Med Microbiol 2012, 61(Pt 1):49-56.
Bartlett JG, Moon N, Chang TW, Taylor N, Onderdonk AB: Role of Clostridium difficile in antibiotic-associated oseudomembranous colitis. Gastroenterology 1978, 75(5):778-782.
Kato H, Kita H, Karasawa T, Maegawa T, Koino Y, Takakuwa H, Saikai T, Kobayashi K, Yamagishi T, Nakamura S: Colonisation and transmission of Clostridium difficile in healthy individuals examined by PCR ribotyping and pulsed-field gel electrophoresis. J Med Microbiol 2001, 50(8):720-727.
Rupnik M, Wilcox MH, Gerding DN: Clostridium difficile infection: new developments in epidemiology and pathogenesis. Nat Rev Microbiol 2009, 7(7):526-536.
Bartlett JG: Clostridium difficile-associated Enteric Disease. Cuff Infect Dis Rep 2002, 4(6):477-483.
Kelly CP: Can we identify patients at high risk of recurrent Clostridium difficile infection? Clin Microbiol Infect 2012, 18 Suppl 6:21-2.
Deneve C, Janoir C, Poilane I, Fantinato C, Collignon A: New trends in Clostridium difficile virulence and pathogenesis. Int J Antimicrob Agents 2009, 33 Suppl 1:S24-2.
Kelly CP, Kyne L: The host immune response to Clostridium difficile. J Med Microbiol 2011, 60(Pt 8):1070-1079.
Kyne L, Warny M, Qamar A, Kelly CP: Association between antibody response to toxin A and protection against recurrent Clostridium difficile diarrhoea. Lancet 2001, 357(9251):189-193.
Bidet P, Lalande V, Salauze B, Burghoffer B, Avesani V, Delmee M, Rossier A, Barbut F, Petit JC: Comparison of PCR-ribotyping, arbitrarily primed PCR, and pulsed-field gel electrophoresis for typing Clostridium difficile. J Clin Microbiol 2000, 38(7):2484-2487.
Pechine S, Janoir C, Collignon A: Variability of Clostridium difficile surface proteins and specific serum antibody response in patients with Clostridium difficile-associated disease. J Clin Microbiol 2005, 43(10):5018-5025.
Tasteyre A, Karjalainen T, Avesani V, Delmee M, Collignon A, Bourlioux P, Barc MC: Molecular characterization of fliD gene encoding flagellar cap and its expression among Clostridium difficile isolates from different serogroups. J Clin Microbiol 2001, 39(3):1178-1183.
Waligora AJ, Hennequin C, Mullany P, Bourlioux P, Collignon A, Karjalainen T: Characterization of a cell surface protein of Clostridium difficile with adhesive properties. Infect Immun 2001, 69(4):2144-2153.
Selby C: Interference in immunoassay. Ann Clin Biochem 1999, 36 ( Pt 6):704-721.
Rousseau C, Poilane I, De Pontual L, Maherault AC, Le Monnier A, Collignon A: Clostridium difficile carriage in healthy infants in the community: a potential reservoir for pathogenic strains. Clin Infect Dis 2012, 55(9):1209-1215.
Lyras D, O'Connor JR, Howarth PM, Sambol SP, Carter GP, Phumoonna T, Poon R, Adams V, Vedantam G, Johnson S et al: Toxin B is essential for virulence of Clostridium difficile. Nature 2009, 458(7242):1176-1179.
Viscidi R, Laughon BE, Yolken R, Bo-Linn P, Moench T, Ryder RW, Bartlett JG: Serum antibody response to toxins A and B of Clostridium difficile. J Infect Dis 1983, 148(1):93-100.
Quinello C, Quintilio W, Carneiro-Sampaio M, Palmeira P: Passive acquisition of protective antibodies reactive with Bordetella pertussis in newborns via placental transfer and breast-feeding. Scand J Immunol 2010, 72(1):66-73.
Al-Jumaili IJ, Shibley M, Lishman AH, Record CO: Incidence and origin of Clostridium difficile in neonates. J Clin Microbiol 1984, 19(1):77-78.
Kelly CP, Pothoulakis C, LaMont JT. Clostridium difficile colitis. N Engl J Med. Jan. 27, 1994;330(4):257-62.
Fekety R. Guidelines for the diagnosis and management of Clostridium difficile-associated diarrhea and colitis. American College of Gastroenterology, Practice Parameters Committee. Am J Gastroenterol May 1997;92(5):739-50.
Wilcox MH. Treatment of Clostridium difficile infection. J Antimicrob Chemother. May 1998;41 Suppl C:41-6.
McFarland LV, Surawicz CM, Rubin M, Fekety R, Elmer GW, Greenberg RN. Recurrent Clostridium difficile disease: epidemiology and clinical characteristics. Infect Control Hosp Epidemiol. Jan. 1999;20(1):43-50.
Fekety R, McFarland LV, Surawicz CM, Greenberg RN, Elmer GW, Mulligan ME. Recurrent Clostridium difficile diarrhea: characteristics of and risk factors for patients enrolled in a prospective, randomized, double-blinded trial. Clin Infect Dis. Mar. 1997;24(3):324-33.
Olson MM, Shanholtzer CJ, Lee JT Jr, Gerding DN. Ten years of prospective Clostridium difficile-associated disease surveillance and treatment at the Minneapolis VA Medical Center, 1982-1991. Infect Control Hosp Epidemiol. Jun. 1994;15(6):371-81.
Do AN, Fridkin SK, Yechouron A, Banerjee SN, Killgore GE, Bourgault AM, Jolivet M, Jarvis WR. Risk factors for early recurrent Clostridium difficile-associated diarrhea. Clin Infect Dis. Apr. 1998;26(4):954-9.
Nair S, Yadav D, Corpuz M, Pitchumoni CS. Clostridium difficile colitis: factors influencing treatment failure and relapse—a prospective evaluation. Am J Gastroenterol. Oct. 1998;93(10):1873-6.
Pechine et al., Journal of Medical Microbiology, 54(2), 2005, 193-196.
Leav. Et al., Vaccine, 28(4), 2010, 965-969.
Voth et al., Clinical Microbiology Reviews, 18(2), 2005, 247-263.
Zar et al., Clinical Infectious Diseases, 45(3), 2007, 302-307.
Vajhi Jafari, Defining innate immunity to Clostridium difficile, 2002.

* cited by examiner

Figure 2

PREDICTIVE VALUE OF *CLOSTRIDIUM DIFFICILE*-SPECIFIC IMMUNE RESPONSE FOR RECURRENCE AND DISEASE OUTCOME

FIELD OF THE INVENTION

The present invention relates to the field of diagnosis, treatment and prevention of recurrent *Clostridium difficile*-Associated Disease.

BACKGROUND OF THE INVENTION

*Clostridium difficile* is responsible of antibiotic-associated diarrhea and pseudomembranous colitis in adults. Over the past 10 years, the incidence and severity of disease have increased in North America and Europe due to the emergence of new PCR ribotypes, such as the 027 strains that have spread worldwide [1]. *C. difficile* infections (CDI) are mainly linked to the use of wide-spectrum antibiotics that disrupt the intestinal microbiota equilibrium [2] [3] [4]. This allows *C. difficile* to multiply and colonize the gut, this being the first step in the pathogenic process. *C. difficile* then produces its toxins, TcdA and TcdB, mediating cell damage, colonic mucosal injury and inflammation, and clinical signs [5]. Asymptomatic colonization with *C. difficile* is common. CDI can range in severity from asymptomatic to severe and life threatening, especially among the elderly [6] [7]. In patients who do develop symptoms, the spectrum of CDI ranges from mild diarrhea to fulminant pseudomembranous colitis.

Most patients with *C. difficile* diarrhea respond well to medical therapy that includes discontinuation of the inciting antibiotic and treatment with metronidazole or vancomycin [20] [21] [22]. However, despite successful treatment of initial episodes, recurrence of diarrhea after withdrawal of specific antibiotherapy is a substantial clinical difficulty. Recurrence rates of 5-65% have been reported, dependent of definition of recurrence and population studied [23]-[27].

The clinical presentations of CDI range from mild self-limited diarrhea to severe life-threatening colitis (Bartlett J G. *Ann Intern Med* 2006; 145(10):758-64). The CDI classification made according to the severity criteria is essential for i) an optimal management of patients, ii) a homogenous categorization of patients in clinical studies, iii) an international comparison of epidemiological data (Bauer M P, et al. *Clin Microbiol Infect* 2009; 15(12):1067-79).

Post-antibiotic diarrhea clinically presents as diarrhea, may be accompanied by lower abdominal pain and systemic symptoms such as mild fever, nausea, and malaise; but there is no significant deterioration of the general health status.

Colitis and pseudomembranous colitis (PMC) clinically presents diffuse or patchy colitis, with or without pseudomembranes, that can be observed on colonoscopy. The characteristic PMC begins with profuse watery diarrhea (>7 stools/day), usually bloodless, often accompanied by fever (>65%), and abdominal pain (70%). Leukocytosis and a biological inflammatory syndrome are common. The histological analysis of these pseudomembranes reveals a superficial necrosis of the mucosa, an exudate accumulation of leukocytes, tissue, debris, and mucus.

Major CDI complications include fulminant colitis, toxic megacolon, perforation, and septic shock syndrome which may be fatal. These complications require medical and surgical treatment (Rupnik M, et al. *Nat Rev Microbiol* 2009; 7(7):526-36).

Mortality associated with mild diarrhea CDI ranges from 0.6 to 1.5% whereas mortality is higher with complications, ranging from 24 to 38%. According to the ECDIS study, one in 10 cases of CDI leads to or contributes to intensive care unit admission or death, or requires total or partial colectomy (Bauer M P, et al. *Lancet* 2011; 377(9759):63-73).

Recurrence is the major clinical issue for CDI. According to the most recent clinical studies, recurrences occur in up to 27% of patients in the month following the first episode (Comely O A, et al. *Lancet Infect Dis* 2012; 12(4):281-9; Louie T J, et al. *N Engl J Med* 2011; 364(5):422-31). Some authors reported that the recurrence rate had increased in recent years (Aslam S, et al. *Lancet Infect Dis* 2005; 5(9):549-57). A patient with recurrence may enter a cycle of multiple recurrences causing exhaustion and protein loss enteropathy (Louie T J, et al. *N Engl J Med* 2011; 364(5):422-31). This cycle is a therapeutic challenge. Recurrences may be due to the intraluminal persistence of *C. difficile* spores (relapses) or to the acquisition of a new strain (reinfection).

Recently, it has been shown that host factors, such as the immune response, play a central role in the pathophysiological process of CDI occurrence or in asymptomatic colonization observed in some patients [8]. CDI is characterized by a high rate of recurrence (~25%) and the frequent occurrence of complications (14%) and mortality related (~4%). The immune status of the host may be involved in recurrent disease, but little is known about the quality of the antibody response associated with effective protection. One study showed that antibody levels against toxins A, B and non-toxin antigens, measured on the third day after the initial onset of diarrhea, were significantly higher in patients who had a single episode of diarrhea than in patients who later developed recurrent CDI [9].

However, one of the limitations of the immunological studies reported in patients with CDI is the lack of a quantitative assay to determine the concentrations of circulating antibodies specific for *C difficile*, and the restricted panel of antigens used to analyze this response.

BRIEF SUMMARY OF THE INVENTION

The invention encompasses an in vitro method of determining a risk for a human subject to develop a *C. difficile*-associated disease (CDAD), a recurrent *C. difficile*-associated disease (CDAD) and/or severe forms of CDAD comprising:
 a) Providing, optionally obtaining, a sample from a human subject,
 b) Quantitating in said sample the level of antibodies specifically binding i) at least one toxin antigen of *C. difficile* and the level of antibodies specifically binding ii) at least one colonization factor antigen of *C. difficile*,
 c) Detecting an increased level of antibodies specifically binding i) at least one toxin antigen of *C. difficile* and ii) at least one colonization factor antigen of *C. difficile* compared to a reference sample or a reference threshold,
wherein an increased level of antibodies in step c) is associated with a low risk of CDAD, recurrent CDAD and/or severe forms of CDAD and,
wherein no increased level of antibodies is step c) is associated with a high risk of CDAD, recurrent CDAD and/or severe forms of CDAD.

The invention also encompasses a method of diagnosing and treating CDAD, recurrent CDAD and/or severe forms of CDAD comprising:

a) Providing, optionally obtaining, a sample from a human subject,
b) Quantitating in said sample the level of antibodies specifically binding i) at least one toxin antigen of *C. difficile* and the level of antibodies specifically binding ii) at least one colonization factor antigen of *C. difficile*,
c) Detecting an increased level of antibodies specifically binding i) at least one toxin antigen of *C. difficile* and ii) at least one colonization factor antigen of *C. difficile* compared to a reference sample or a reference threshold, wherein an increased level of antibodies in step c) is associated with a low risk of CDAD, recurrent CDAD and/or severe forms of CDAD and,
wherein no increased level of antibodies is step c) is associated with a high risk of CDAD, recurrent CDAD and/or severe forms of CDAD, d) Administering to said high risk human subject a treatment against *C. difficile* infection.

The invention also encompasses a method of preventing CDAD, recurrent CDAD and/or severe forms of CDAD in a human subject comprising:
a) Providing, optionally obtaining, a sample from a human subject,
b) Quantitating in said sample the level of antibodies specifically binding i) at least one toxin antigen of *C. difficile* and the level of antibodies specifically binding ii) at least one colonization factor antigen of *C. difficile*,
c) Detecting an increased level of antibodies specifically binding i) at least one toxin antigen of *C. difficile* and ii) at least one colonization factor antigen of *C. difficile* compared to a reference sample or a reference threshold, wherein an increased level of antibodies in step c) is associated with a low risk of CDAD, recurrent CDAD and/or severe forms of CDAD and,
wherein no increased level of antibodies is step c) is associated with a high risk of CDAD, recurrent CDAD and/or severe forms of CDAD, d) Administering to said high risk human subject an immunogenic composition against *C. difficile* infection.

The invention also encompasses a kit for determining in vitro a risk for a human subject to develop CDAD, recurrent CDAD and/or severe forms of CDAD comprising:
a) Antigens as defined in the present invention, bound to a solid support,
b) Labelled antibodies directed against human IgG, IgA and/or IgM.

BRIEF DESCRIPTION OF THE DRAWINGS

Figure 2:
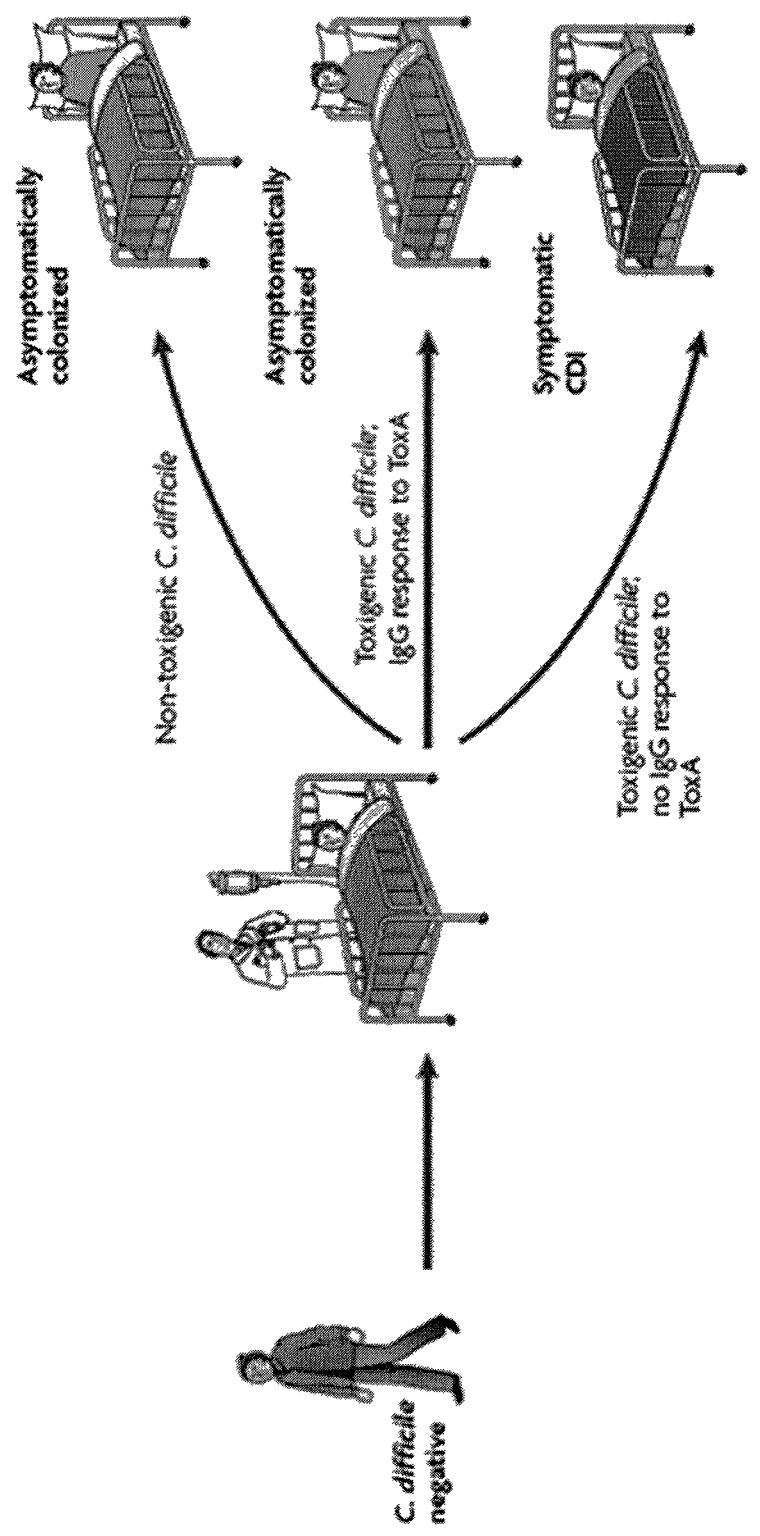

FIG. 2 depicts a model for the acquisition of *C. difficile* infection (Rupnik et al. 2009).

DETAILED DESCRIPTION OF THE INVENTION

Figure 1:
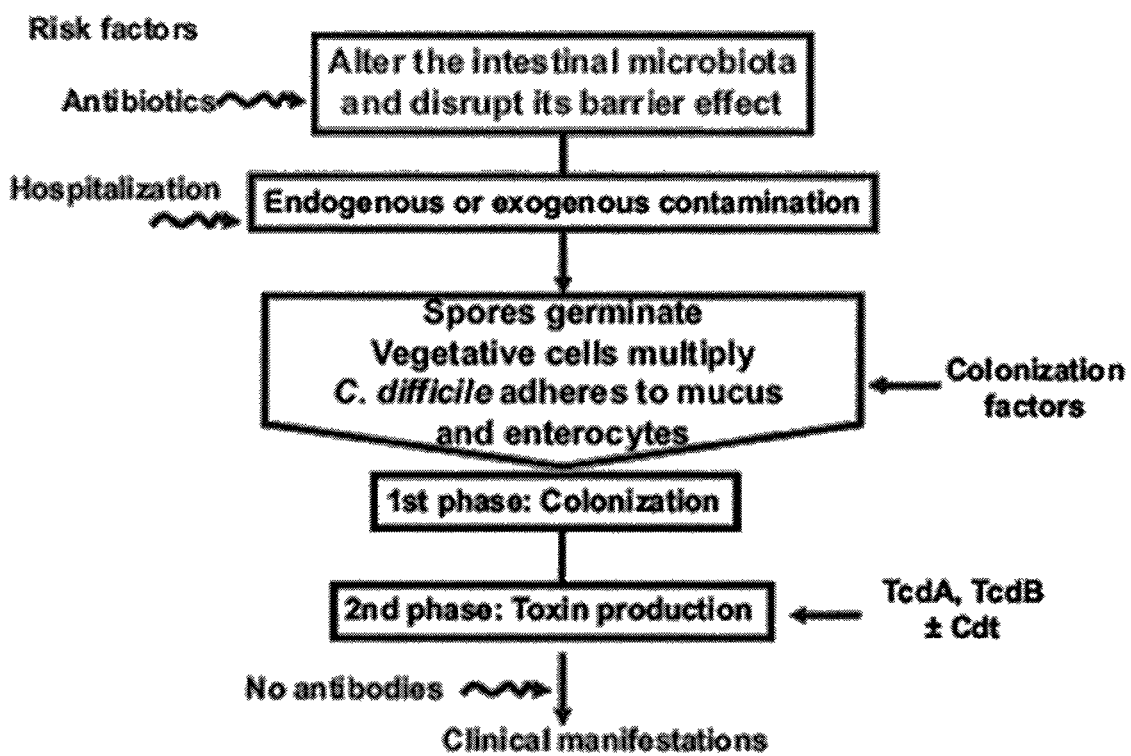
FIG. 1 depicts the pathogenesis of *Clostridium difficile*.

In the present invention, we addressed the question of the immune parameters that may be associated with recurrent CDI and/or severe forms of CDAD, using a quantitative assay that we developed to assess the antibody response against a pattern of antigens combining colonization factors and toxin A (TcdA) and toxin B (TcdB) of *C difficile*.

A first object of the invention relates to an in vitro method of determining or diagnosing a risk for a human subject to develop *C. difficile*-associated disease (CDAD), recurrent CDAD and/or severe forms of CDAD, said method comprising:
  a) Providing, optionally obtaining, a sample from a human subject,
  b) Quantitating in said sample the level of antibodies specifically binding i) at least one toxin antigen of *C. difficile* and the level of antibodies specifically binding ii) at least one colonization factor antigen of *C. difficile*, and
  c) Comparing said level of antibodies to a reference sample or a reference threshold.

In this method, an increased level of antibodies in step c) is associated with a low risk of developing a CDAD, a recurrent CDAD and/or severe forms of CDAD and no increased level of antibodies in step c) is associated with a high risk of developing a CDAD, a recurrent CDAD and/or severe forms of CDAD.

As used herein, "CDAD" stands for "*C. difficile*-associated disease" and is synonymous of *C. difficile* infections (CDI). In the present invention, "CDAD" designates mild-form of CDIs, such as diarrhea, post-antibiotic diarrhea, colitis, or pseudomembranous colitis. When they occur repeatedly in the same patient (for example two times within the same month), these symptoms unravel a "recurrent CDAD". "Severe forms of CDAD" include, but are not limited to, fulminant colitis, toxic megacolon, megacolon perforation, and septic shock.

As disclosed herein, the term "in vitro" refers to studies or experiments that are conducted using biological samples (e.g., blood or serum samples) which have been isolated from their host organisms (e.g., animals or humans). These experiments can be for example reduced to practice in laboratory materials such as tubes, flasks, wells, microtubes, etc. In contrast, when used herein, the term "in vivo" refers to studies that are conducted on whole living organisms.

In the present application, the term "quantitating" encompasses the term "quantifying" and any suitable informative determination of specific antibodies.

As used herein, the term "reference sample" or "reference threshold" refers to the level of antibodies in a subject negative for *C. difficile*. Preferably, said reference sample or reference threshold refers to the level of antibodies in the subject undergoing a method of the invention prior to the development of CDAD in said subject. More preferably, said reference sample has been obtained from a subject or a group of subjects that have never been infected by *C. difficile*, so that said sample does not contain any antibody against *C. difficile* antigens. In this case, the reference threshold is therefore close to zero.

In the context of the invention, the term "specifically" or "specific" means that the antibodies or their fragments are able to recognize and to bind only its target antigen. More precisely, in the context of the present invention, an antibody is said to "specifically bind" or to "specifically recognize" a peptide if said antibody has an affinity constant $K_a$ higher than $10^6$ $M^{-1}$, preferably higher than $10^7$ $M^{-1}$, more preferably higher than $10^9$ $M^{-1}$ for said peptide and has an affinity constant $K_a$ lower than $10^4$ $M^{-1}$ for all the other peptide.

In the present application, unless otherwise stated, description relating to antibodies applies to their fragments as disclosed above.

The term "antibody" as used herein is intended to include monoclonal antibodies, polyclonal antibodies, and chimeric antibodies. Preferably, the antibodies which are to be detected by the immunoassays of the invention are polyclonal antibodies, which are present in biological samples of diseased patients, and have therefore been generated from different B cell sources. As such, they recognize different epitopes exhibited by a pathogenic antigen (on the other hand, monoclonal antibodies are derived from a single cell line and recognize the same epitope).

An antibody (or "immunoglobulin") consists of a glycoprotein comprising at least two heavy (H) chains and two light (L) chains inter-connected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed "complementarity determining regions" (CDR) or "hypervariable regions", which are primarily responsible for binding an epitope of an antigen, and which are interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

Antibody can be of different isotypes (namely IgA, IgD, IgE, IgG or IgM). IgA, IgG and IgM type antibodies can be detected by the present method. Of note, these isotypes are composed of two identical heavy chains and two identical light chains that are joined by disulfide bonds. Importantly, IgM antibodies form polymers where multiple immunoglobulins are covalently linked together with disulfide bonds, mostly as a pentamer but also as a hexamer, so that they have a molecular mass of approximately 900 kDa (in their pentamer form). Because each monomer has two antigen binding sites, a pentameric IgM has 10 binding sites. Typically, however, IgM antibodies cannot bind 10 antigens at the same time because the large size of most antigens hinders binding to nearby sites. Due to its polymeric nature, IgM possesses high avidity.

Antibody fragments can also be detected thanks to the present method. This term is intended to include Fab, Fab', F(ab')2, scFv, dsFv, ds-scFv, dimers, minibodies, diabodies, and multimers thereof and bispecific antibody fragments.

Monoclonal antibodies can be used in the present immunoassays; for example for detecting the immunoglobulins that are bound to the solid supports. As used herein, "monoclonal antibody" defines an antibody arising from a homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen.

The term "antigen" herein means any substance that causes the immune system to produce antibodies against the said substance. An "immunogenic" antigen is a specific type of antigen which is able to stimulate an adaptive immune response if injected on its own. At the molecular level, an antigen is thus characterized by its ability to be "bound" to the antigen-binding site of an antibody.

In the context of the present invention, the antigens used in the methods of the invention are *C. difficile* antigens. Preferably, they are *C. difficile* toxin antigens such as TcdA and TcdB and/or *C. difficile* colonization factor antigens such as FliD and Cwp84.

In the context of the present invention, an antibody is said to "bind" a define antigen (or epitope) or to "recognize" said antigen (or epitope) if said antibody has an affinity constant $K_a$ (which is the inverted dissociation constant, i.e. $1/K_d$) higher than $10^5$ $M^{-1}$, preferably higher than $10^6$ $M^{-1}$, more preferably higher than $10^7$ $M^{-1}$ for said antigen (or epitope). This affinity can be measured for example by equilibrium dialysis or by fluorescence quenching, both technologies being routinely used in the art.

In a preferred embodiment, the method of the invention is carried out by an ELISA assay.

An ELISA (Enzyme-Linked Immunosorbent Assay) assay requires the use of antigens as described in the present invention, said antigens being immobilized on a solid support, preferably a microtiter plate. An ELISA assay according to the invention is disclosed in the experimental part of the application. ELISA assays are broadly used and well-described in the art.

Of note, the detection of the analytes (e.g., the antibodies of the invention) is enhanced by adjusting the amount of detergent present in the buffers used in the immunoassay (washing, coating and/or dilution buffers). A poor concentration of detergent will indeed favor unspecific binding, matrix effects, and/or cross reactivity with interference substances that are present in the analyzed samples.

To avoid occurrence of these interferences, it is for example possible to use sodium deoxycholate as detergent, in a concentration from 0.1% to 0.18%. The skilled person will be capable to adjust this amount to each antibody to detect. It is also possible to use Tween20® at concentrations of 0.1%-0.5%.

In a preferred embodiment, 0.18% of sodium deoxycholate is used in buffers for anti-FliD Ig detection and 0.14% of sodium deoxycholate is used in the buffers for anti-Cwp84, anti-TcdA and anti-TcdB Ig detection. More precisely, 0.18% of sodium deoxycholate can be used in the coating buffer for anti-FliD Ig detection and 0.14% of sodium deoxycholate can be used in the coating buffer for anti-Cwp84 Ig detection.

In another preferred embodiment, 0.1% of Tween20® is used in the buffers for anti-FliD, anti-TcdA and anti-TcdB Ig detection and 0.5% of Tween20® is used in the buffers for anti-Cwp84 Ig detection. More precisely, 0.1% of Tween20® can be used in the washing buffer and/or dilution buffer for anti-FliD, anti-TcdA and anti-TcdB Ig detection, for all antibody isotypes. 0.5% of Tween20® can be used in the washing buffer and/or dilution buffer for anti-Cwp84 IgG and IgM detection. Yet, 0.1% of Tween20® is preferably used in the dilution buffer for anti-Cwp84 IgA detection.

The most preferred characteristics are summarized in table 1 below:
For anti-FliD Ig detection (all isotypes): 0.18% of sodium deoxycholate is used in coating buffer, then 0.5% of Tween20® is used in the washing and dilution buffers,
For anti-TcdA Ig detection (all isotypes): 0.14% of sodium deoxycholate is used in coating buffer, then 0.1% of Tween20® is used in the washing and dilution buffers,
For anti-TcdB Ig detection (all isotypes): 0.14% of sodium deoxycholate is used in coating buffer, then 0.1% of Tween20® is used in the washing and dilution buffers,
For anti-Cwp84 IgG and IgM detection (IgG and IgM): 0.14% of sodium deoxycholate is used in coating buffer, then 0.5% of Tween20® is used in the washing and dilution buffers,
For anti-Cwp84 IgA detection (IgA): 0.14% of sodium deoxycholate is used in coating buffer, then 0.5% of Tween20® is used in the washing buffer, and 0.1% of Tween20® is used in the dilution buffer.

The method of the invention, and in particular the ELISA assay of the invention, comprises a step of detecting the human immunoglobulins bound to the immobilized antigens. This detection is typically performed with a revealing agent. This "revealing agent" can be an antibody or a functional fragment of same, either in the form of an immunoconjugate, or a labeled antibody in order to obtain a detectable and/or quantifiable signal.

In a preferred embodiment, said revealing agent is preferably an anti-human IgM, an anti-human IgA or an anti-human IgG antibody, more preferably conjugated with a detectable label. Examples of detectable labels include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorot[pi]azinylamine fluorescein, dansyl chloride or phycoerythrin; example of luminescent material includes luminol, and examples of bioluminescent materials include luciferase, luciferin, and aequorin; examples of suitable radioactive material include $^{125}I$, $^{131}I$, $^{35}S$ or $^{3}H$.

It is also possible to use the antigen of the invention coupled with beads or nanoparticles. Coated beads or nanoparticles carrying the antigen of the invention would aggregate or immunocaptured in the presence of a subject's serum containing antibodies recognizing this antigen. This aggregation is easily detectable by conventional means, such as by microscopy, by flow cytometer, or naked eyes, etc.

The diagnostic assays of the invention advantageously contain a positive control to which the revealing agent binds without requiring the presence of the antigen—human immunoglobulin complexes. For example, if the revealing agent is anti-human IgM antibody, the positive control can consist in human IgM or at least the constant part thereof.

Other methods of detection of antibodies suitable for the purpose of the present invention are well known by the skilled artisan.

In a preferred embodiment, the method of the invention further comprises a step of isolation and identification of a bacterial strain. Preferably, said bacterial strain is a toxigenic *C. difficile*. As a matter of fact, if toxigenic *C. difficile* bacteria are detected in a subject that is devoid of antibodies recognizing *C. difficile* toxins, this indicates that the immune system of said subject is deficient and that recurrent and/or severe forms of CDAD will certainly develop.

Methods of isolating an identifying *C. difficile* are well known to the skilled artisan. Such methods are disclosed in Eckert C. et al. *Clostridium difficile* infection diagnosis. Journal des Anti-infectieux 2011, vol. 13, No. 2, p. 67-73.

In a preferred embodiment, the human subject is a person at risk of developing a CDAD. In a more preferred embodiment, said human subject is selected from the group comprising: elderly person, pregnant woman, newborn and innate or acquired immunodeficient person.

In another preferred embodiment, the human subject is diagnosed with a CDAD. For example, it is a pregnant woman diagnosed with a CDAD.

In another preferred embodiment, said human subject is a newborn. Preferably, said newborn has a mother diagnosed with a CDAD.

Preferably, said newborn is (or has been) breastfed.

Alternatively, said newborn may not have been breastfed.

In a particular embodiment, said subject is a patient infected with *C. difficile*, or having a symptom of *C. difficile*-associated disease ("CDAD"; e.g., diarrhea, colitis, abdominal pain) or a predisposition towards *C. difficile*-associated disease (e.g., undergoing treatment with antibiotics, or having experienced *C. difficile*-associated disease and at risk for relapse of the disease). In addition, patients taking stomach ulcer drugs, known as proton pump inhibitors, are at increased risk for contracting *C. difficile* infection.

In a preferred embodiment, the toxin antigen is selected from the group comprising TcdA and TcdB and the colonization factor antigen is selected in the group comprising Cwp84 and FliD.

The term "toxin A" or "TcdA" refers to the toxin A protein encoded by *C. difficile*. Preferably, it refers to the TcdA protein of *C. difficile* strain VPI10463 having the GenBank reference AAA23283.

"Toxin B" or "TcdB" refers to the toxin B protein encoded by *C. difficile*. Preferably, it refers to the TcdB protein of *C. difficile* strain VPI10463 having the Swiss Prot reference P18177.

"Protein" is used interchangeably with "polypeptide."

Toxin A is an enterotoxin with minimal cytotoxic activity, whereas toxin B is a potent cytotoxin but has limited enterotoxic activity. The extensive damage to the intestinal mucosa is attributable to the action of toxin A, however, toxins A and B act synergistically in the intestine.

Flagellar protein FliD and Cell Wall protein 84 Cwp84 are *C. difficile* surface proteins. These proteins bind to gastrointestinal tissues and are colonization factors.

Preferably, the "FliD" protein referred to in this application is the FliD protein of *C. difficile* strain 79-685 having the GenBank reference AAK18784.1 (Tasteyre et al. *J Clin Microbiol*. 2001 March; 39(3):1178-83).

Preferably, the "Cwp84" protein referred to in this application is the Cwp84 protein of *C. difficile* strain 79-685 having the GenBank reference AAO61257.1 (Savariau-Lacomme et al. *J Bacteriol*. 2003 August; 185(15):4461-70).

In a more preferred embodiment, the colonization factor antigen is FliD and/or Cwp84 and the toxin antigens are TcdA and/or TcdB.

For example, the colonization factor is FliD and the toxin antigen is TcdA, or the colonization factor is Cwp84 and the toxin antigen is TcdA, or the colonization factor is FliD and the toxin antigen is TcdB, or the colonization factor is Cwp84 and the toxin antigen is TcdB.

More preferably, the antibodies specifically binding at least the colonization factors FliD and Cwp84 and the toxin antigen TcdA are detected.

More preferably, the antibodies specifically binding at least the colonization factors FliD and Cwp84 and the toxin antigen TcdB are detected.

More preferably, the antibodies specifically binding at least the colonization factor FliD and the toxin antigens TcdA and TcdB are detected.

More preferably, the antibodies specifically binding at least the colonization factor Cwp84 and the toxin antigens TcdA and TcdB are detected.

More preferably, the antibodies specifically binding at least the colonization factors FliD and Cwp84 and the toxin antigens TcdA and TcdB are detected.

In a preferred embodiment, antibodies of the IgG isotype are detected.

In this preferred embodiment, when the level of IgG specifically binding FliD is at least 1.86 µg/mL, the patient is classified as low risk of CDAD, recurrent CDAD and/or severe forms of CDAD.

In this preferred embodiment, when level of IgG specifically binding TcdA is at least 0.38 µg/mL, the patient is classified as low risk of CDAD, recurrent CDAD and/or severe forms of CDAD.

In this preferred embodiment, when level of IgG specifically binding TcdB is at least 1.56 µg/mL, the patient is classified as low risk of CDAD, recurrent CDAD and/or severe forms of CDAD.

In this preferred embodiment, when the level of IgG specifically binding FliD is at least two times higher, compared to the reference sample or to the reference threshold, the patient is classified as low risk of CDAD, recurrent CDAD and/or severe forms of CDAD.

In this preferred embodiment, when the level of IgG specifically binding TcdA is at least five times higher, compared to the reference sample or to the reference threshold, the patient is classified as low risk of CDAD, recurrent CDAD and/or severe forms of CDAD.

In this preferred embodiment, when the level of IgG specifically binding TcdB is at least five times higher, compared to the reference sample or to the reference threshold, the patient is classified as low risk of CDAD, recurrent CDAD and/or severe forms of CDAD.

Preferably, said IgG level is detected in non-breastfed newborns.

In a preferred embodiment, antibodies of the IgA isotype are detected, especially when the tested subject is a breastfed newborn.

More preferably, antibodies of the IgA isotype specifically binding FliD and antibodies of the IgA isotype specific for Cwp84 are detected in breastfed newborns, more preferably in lactoserum given to breastfed newborns. All the above-mentioned combinations are also useful.

In a preferred embodiment, antibodies of the IgM isotype are detected.

More preferably, antibodies of the IgM isotype specifically binding FliD are detected.

When the level of IgM specifically binding FliD is at least two times higher compared to the reference sample or to the reference threshold, the patient is classified as low risk of CDAD, recurrent CDAD and/or severe forms of CDAD.

In a preferred embodiment, if the level of IgM specifically binding FliD is at least 0.65 µg/mL, the patient is classified as low risk of CDAD, recurrent CDAD and/or severe forms of CDAD.

In a preferred embodiment, antibodies of the IgG isotype specifically binding FliD, TcdA and/or TcdB respectively and antibodies of the IgM isotype specifically binding FliD, are detected.

As used herein, the term "biological sample" or "sample" refers to any samples which have been obtained from a patient and which might contain antibodies. Preferably, said biological sample is a biological fluid, for example an unfiltered biological fluid such as urine, cerebrospinal fluid, pleural fluid, synovial fluid, peritoneal fluid, amniotic fluid, gastric fluid, blood, serum, lactoserum, plasma, lymph fluid, interstitial fluid, saliva, physiological secretions, tears, mucus, sweat, milk, semen, seminal fluid, vaginal secretions, fluid from ulcers and other surface eruptions, blisters, and abscesses. It also refers to an extract of tissues including biopsies of normal, malignant, and suspect tissues or any other constituents of the body which may contain antibodies. The said biological sample can be pre-treated prior to use, such as preparing plasma from blood, diluting viscous fluids, or the like; methods of treatment can involve filtration, distillation, concentration, inactivation of interfering compounds, and the addition of reagents.

In a preferred embodiment, the sample is selected from the group comprising: blood, cord blood, lactoserum, saliva and feces.

In a preferred embodiment, antibodies of the IgA isotype specifically binding FliD and/or antibodies of the IgA isotype specific for Cwp84 are detected in lactoserum.

Another object of the invention relates to a method of treating and/or preventing recurrent CDAD and/or severe forms of CDAD comprising:
  a) Providing, optionally obtaining, a sample from a human subject
  b) Quantitating in said sample the level of antibodies specifically binding i) at least one toxin antigen of C. difficile and ii) at least one colonization factor antigen of C. difficile,
  c) Comparing said level of antibodies to a reference sample or a reference threshold,
  d) Administering to said high risk human subject a treatment or an immunogenic composition against C. difficile infection when no increased level of antibodies is observed in step c).

In a preferred embodiment, the treatment is a preventive treatment or a curative treatment.

In a preferred embodiment, the curative treatment consists in administering an antibiotic, preferably the antibiotic is selected from the group comprising metronidazole, vancomycin, teicoplanin, bacitracin, fusidic acid and tigecyclin. (Barbut et al., Treatment of *Clostridium difficile* infections: old and new approaches, Journal des anti-infectieux, 2011, vol. 13 No. 2, p. 74-86).

In a preferred embodiment, the preventive treatment consists in administering an immunogenic composition, preferably a vaccine.

Said vaccine can be a prophylactic vaccine or a therapeutic vaccine, as those disclosed in Mizrahi A. et al, *Anaerobe* 30 (2014) 210-219.

Preferred vaccines for example contain *C. difficile* toxins (such as TcdA and TcdB toxins), or *C. difficile* colonization factors such as S layer proteins (Sip), flagellar proteins such as FliD, or Cwp84 protease.

The present invention also relates to the said preventive or curative treatment for use for preventing and/or treating CDAD, recurrent CDAD and/or severe forms of CDAD in a human subject in need thereof, by example in a human subject that has been diagnosed to have a high risk of developing CDAD, recurrent CDAD and/or severe forms of CDAD by the diagnosing method of the invention (see above).

As used herein, the term "administer" and "administering" are used to mean introducing the antibiotic or the immunogenic composition into a subject. When administration is for the purpose of treatment, the substance is provided at, or after the onset of, a symptom of a bacterial infection. The therapeutic administration of this substance serves to attenuate any symptom, or prevent additional symptoms from arising. When administration is for the purposes of preventing or reducing the likelihood a bacterial infection or a recurrent ("prophylactic administration"), the substance is provided in advance of any visible or detectable symptom, such as after the symptoms of the initial infection. The prophylactic administration of the substance serves to attenuate subsequently arising symptoms or prevent or reduce the likelihood of the symptoms from arising altogether.

When the detection step reveals that the biological sample contains low levels of human immunoglobulins that are specific to the antigens of the invention, the said subject is diagnosed to be at high risk of developing recurrent CDAD. It is then possible to administer an appropriate antibiotic treatment and/or a preventive treatment.

In a preferred embodiment, said method of treatment and/or prevention further comprises a step of isolation and identification of a bacterial strain, preferably said bacterial strain is a toxigenic C. difficile.

In a preferred embodiment, said method further comprises repeating steps b) and c).

In a preferred embodiment, the sample is selected from the group comprising blood, cordblood, lactoserum, saliva or feces.

In a preferred embodiment, the human subject is a person at risk of developing a CDAD, preferably selected from the group comprising elderly person, pregnant woman, newborn and innate or acquired immunodeficient person. In another preferred embodiment, said human subject is diagnosed with a CDAD. In a more preferred embodiment, said human subject is a pregnant woman diagnosed with a CDAD.

In a more preferred embodiment, the human subject is a newborn having a mother diagnosed with a CDAD.

In a more preferred embodiment, the human subject is a newborn that has been breastfed or not.

The invention thus relates to a method for identifying in vitro if a subject will benefit from the preventive treatment against CDAD or recurrent CDAD, the method comprising:
a) conducting the diagnosis method of the invention on a biological sample of said subject, as defined above, and
b) identifying if the subject will benefit from the preventive treatment if the said biological sample contains low levels of human immunoglobulins that are specific for the antigens defined above.

As meant herein, a subject is identified as to benefit from the preventive treatment if it is diagnosed to be at risk of developing CDAD, recurrent CDAD and/or severe forms of CDAD by the diagnosis method of the invention.

Another object of the invention relates to a kit for diagnosing or determining in vitro a risk for a human subject to develop CDAD, recurrent CDAD and/or severe forms of CDAD, said kit comprising:
c) At least one, preferably two, more preferably three and even more preferably four antigen, as defined above, bound to a solid support, and
d) Labelled antibodies directed against human IgG, IgA and/or IgM.

The kits of the invention generally comprise a solid support coated with antigens as described above and a revealing agent.

In a preferred embodiment, the kit of the invention further comprises a solution to preserve antibodies from the sample, wherein said sample is selected in the group comprising lactoserum, cordblood, blood, saliva or feces.

In a preferred embodiment, the said revealing agent is a labeled antibody, more preferably a labeled anti-human IgM antibody. Examples of detectable labels include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorot[pi]azinylamine fluorescein, dansyl chloride or phycoerythrin; example of luminescent material includes luminol, and examples of bioluminescent materials include luciferase, luciferin, and aequorin; examples of suitable radioactive material include $^{125}$I, $^{131}$I, $^{35}$S or $^{3}$H.

In a preferred embodiment, the solid support of said kit is a microtiter plate or a nitrocellulose membrane.

In a preferred embodiment, the kit of the invention further comprises a control sample which is also recognized by said revealing agent. For example, if the revealing agent is an anti-human IgM antibody, the positive control can consist in human IgM or at least the constant part thereof.

In a preferred embodiment, the kit of the invention further comprises a washing buffer and/or a dilution buffer. In a more preferred embodiment, washing and/or dilution buffers contain 0.1% of Tween20® for anti-FliD, anti-TcdA and anti-TcdB Ig detection and 0.5% of Tween20® for anti-Cwp84 Ig detection. More precisely, washing buffer and/or dilution buffer for anti-FliD, anti-TcdA and anti-TcdB Ig detection, for all antibody isotypes contain 0.1% of Tween20; washing buffer and/or dilution buffer for anti-Cwp84 IgG and IgM detection contain 0.5% of Tween20®, and dilution buffer for anti-Cwp84 IgA detection contains 0.1% of Tween20®.

The kits of the invention can also include instructions for interpreting the results obtained using the kit.

Kits may also comprise, e.g., a buffering agent, a preservative, or a protein stabilizing agent. The kits can further comprise components necessary for detecting the detectable label (e.g., an enzyme or a substrate). Each component of a kit can be enclosed within an individual container and all of the various containers can be within a single package, along with instructions for interpreting the results of the assays performed using the kit.

In another aspect, the present invention relates to the use of the kit of the invention for diagnosing or determining in vitro a risk for a human subject to develop CDAD, recurrent CDAD and/or severe forms of CDAD.

In a preferred embodiment, said human subject is a person at risk of developing a CDAD, preferably selected from the group comprising elderly person, pregnant woman, newborn, and innate or acquired immunodeficient person. Preferably said person at risk is a pregnant woman. Preferably, said pregnant woman is diagnosed with a CDAD.

In a more preferred embodiment, the human subject is a newborn having a mother diagnosed with a CDAD. Preferably, said newborn is not breastfed.

In one embodiment, the kit comprises:
a) FliD and TcdA and/or TcdB antigens bound to a solid support,
b) Labelled antibodies directed against human IgG and/or IgM.

In one embodiment, the kit comprises a FliD antigen bound to a solid support and a labeled antibody directed against human IgG and/or IgM.

In one embodiment, the kit comprises:
a) At least one, preferably two colonization factor antigen(s) selected in the group comprising Cwp84 and FliD, said antigen(s) being bound to a solid support,
b) At least one, preferably two, toxin antigen(s) selected from the group comprising TcdA and TcdB, said antigen being bound to a solid support.

In a preferred embodiment, the kit comprises the colonization factor antigens Cwp84, FliD, and the toxins TcdA and TcdB, said antigens being bound to a solid support.

The invention further comprises a method for generating a kit for the detection of C. difficile comprising coating a solid support with an antigen of the invention, preferably a FliD, TcdA, and/or TcdB antigen, in the presence of deoxycholate at 0.13%, 0.14%, 0.15%, 0.16%, 0.17%, 0.18%, 0.19%, or 0.20%.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Examples

1. Methods 1.1. Study Design, Subject Recruitment and Samples

Figure 3:
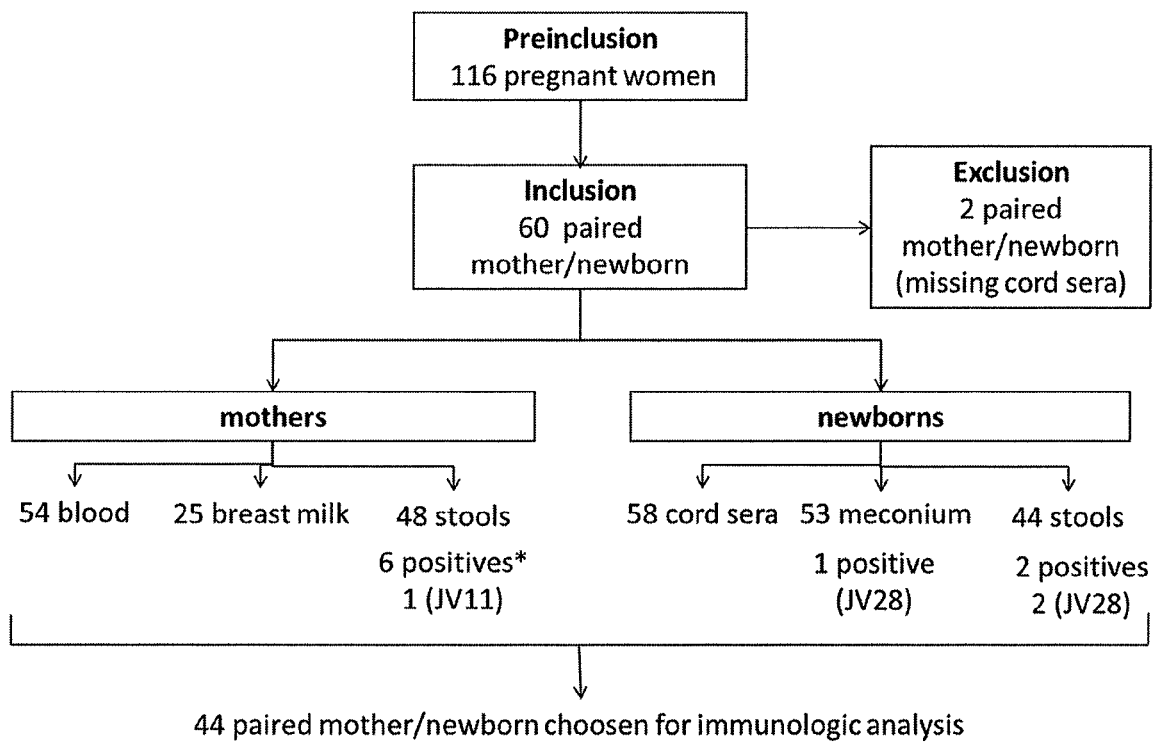
FIG. 3 depicts the flowchart of the study.

In the context of a prospective study designed to demonstrate the passive acquisition of antibodies against *C. difficile* in newborns via placental transfer and breast-feeding, pregnant women were pre-included during their last pregnancy consultation and gave a written informed consent if they accepted to participate to the study. During delivery, mothers and their newborn were included (FIG. 3). The exclusion criteria were women under 18 years old, HIV-infected women, or women who were blood transfused during the last month before delivery. The Institutional Review Board (Comité de Protection des Personnes Ile de France) approved the study. Umbilical cord blood from newborns, blood and breast milk from their mothers were collected, centrifuged, aliquoted and frozen at −80° C. To identify the risk factors on an early carriage in newborns, meconium and newborn stools were sampled, as well as maternal stools that were collected during the peripartum (FIG. 1). In addition, 12 age-matched volunteer healthy women and 12 age-matched women infected by *C. difficile* were included. Sera from these subjects were kept at −80° C. A questionnaire about clinical and environmental data that may favor *C. difficile* colonization was completed by the maternity staff.

1.2. Detection, Identification and Molecular Typing of *C. difficile*

Isolation of *C. difficile* from fresh meconium and stools from newborns and from their mothers was done using the reference method as follows: stool samples were cultured on three different media: a selective media (CLO-BioMérieux), a chomogenic media (ChromID®*C. difficile*, BioMérieux) and a sporulating media with agar supplemented with 10% horse blood, 0.1% sodium taurocholate (CCTa), 8 mg/L cefoxitin and 250 mg/L cycloserin. Cultures were incubated for 48 h at 37° C. *C. difficile* colonies were characterized according to their characteristic morphology in culture, smelling and yellow fluorescence at 360 nm, and *C. difficile* was identified with Gram staining and Vitek® (BioMérieux) and MALDI-TOF-MS (MALDI Biotyper, Brücker Daltonics). The presence of toxins A and B was searched by enzyme immunoassay (*C. difficile* Quik Chek Complete®, Alere). The isolates were characterized by PCR-Ribotyping as described by Bidet et al. [10].

1.3. Antigen Production and Purification

Toxin A and B were provided by the Centre National de Reference des bactéries anaérobies et toxines at Institut Pasteur, directed by Dr. Michel R. Popoff. Recombinant FliD and the cysteine protease Cwp84 from *C. difficile* strain 79-685 were produced as previously described [11] [12] [13]. Briefly, *E. coli* BL21/pGEX-6P-1 clone that expresses FliD and *E. coli* BL21/pET-28a(+)_cwp84$_{30-803}$ clone that expresses the whole Cwp84 (without the peptide signal), were seeded in Luria-Bertani (Becton Dickinson) medium supplemented with 100 mg/ml ampicillin (Sigma) and 50 µg/ml kanamycin. Protein expression was induced with 1 mM of IPTG (isopropyl β-D-thiogalactopyranoside. Cultures were incubated 16 h at 20° C. for FliD and 4 h at 37° C. for Cwp84. Single step protein purification was performed by affinity chromatography using a glutathione Sepharose 4B (GE Healthcare) for FliD and a cobalt affinity resin (Jena BioScience) for Cwp84. The proteolytic activity of Cwp84 was checked as previously described [11].

1.4. Quantitative ELISA for FliD-, Cwp84-, TcdA- and TcdB-Specific Antibody Responses 96-well plates (MaxiSorp, Nunc) were coated overnight at 37° C. with 100 µl of either FliD (0.5 µg/ml), Cwp84 (0.9 µg/ml), TcdA (0.1 µg/ml) or TcdB (0.2 µg/ml) diluted in the coating buffer (carbonate/bicarbonate 0.1% v/v sodium deoxycholate, pH 9.6). Plates were then washed with the washing buffer (PBS containing 0.1 to 0.5% (v/v) Tween®20 (Sigma) to remove unbound antigen. Unsaturated sites were blocked with 200 µl of the saturating buffer (PBS 3% BSA) 1 h at 37° C. Serum to be tested were diluted with the Multiprobe II® robot in the dilution buffer (PBS 1% BSA 0.1 to 0.5% (v/v) Tween®20), 100 µl of diluted serum were added in each well and incubated 1 h at 37° C. The plates were washed with the washing buffer. Goat anti-human IgG, IgA or IgM alkaline phosphatase-conjugated antibodies were added and antigen-specific antibodies detected with para-nitrophenyl phosphate (pNPP) substrate. The reaction was then stopped by 100 µl of sodium hydroxide and the optical density read at 405 nm.

The calibration curves were set up using purified polyclonal human IgG, IgA and IgM (Sigma). The wells were coated with serial dilutions of the corresponding isotypes starting with the concentration of 0.96 µg/ml for IgG, 1.6 µg/ml for IgA, and 0.6 µg/ml for IgM. The assay was then performed as described above, and the concentrations of serum antibodies were calculated according to the calibration curves (see below). The ELISA data are expressed in µg/ml.

1.5. Statistical Analyses

The Mann-Whitney rank sum test was used for comparison between the different groups of patients. Correlations were tested by the Spearman rank correlation, and linear regression analysis was effected. Correlations were considered significant at $p<0.05$.

2. Results 2.1. Description of the Paired Mother/Newborn Population Selected for the Immunologic Study 44 paired mother/newborn were selected (FIG. 3). The median age was 32 years old (range 20 to 41 years). Two risk factors for *C. difficile* carriage were registered i.e caesarean (n=7, 16%) and antibiotic treatment during delivery (n=14, 32%). Among the 44 mothers, 5 (11%) were *C. difficile* carriers, 36 (82%) non *C. difficile* carriers, and 3 (7%) were undetermined (lost samples or not done). All the strains isolated during the study were non-toxinogenic *C. difficile*.

Regarding newborns (16 girls and 28 boys), all were born at full term. Mean weight was 3.4 kg, and mean duration of stay in the maternity was four days (2 to 10 days). Three newborns (7%) received an antibiotic treatment, and 31 (70%) were breast-fed.

2.2. Development and Optimization of the Quantitative ELISA Assay for the Detection of Antibodies Against *C. difficile* Surface Antigens and Toxins in Serum, Lactoserum and Cord Blood.

Figure 4:
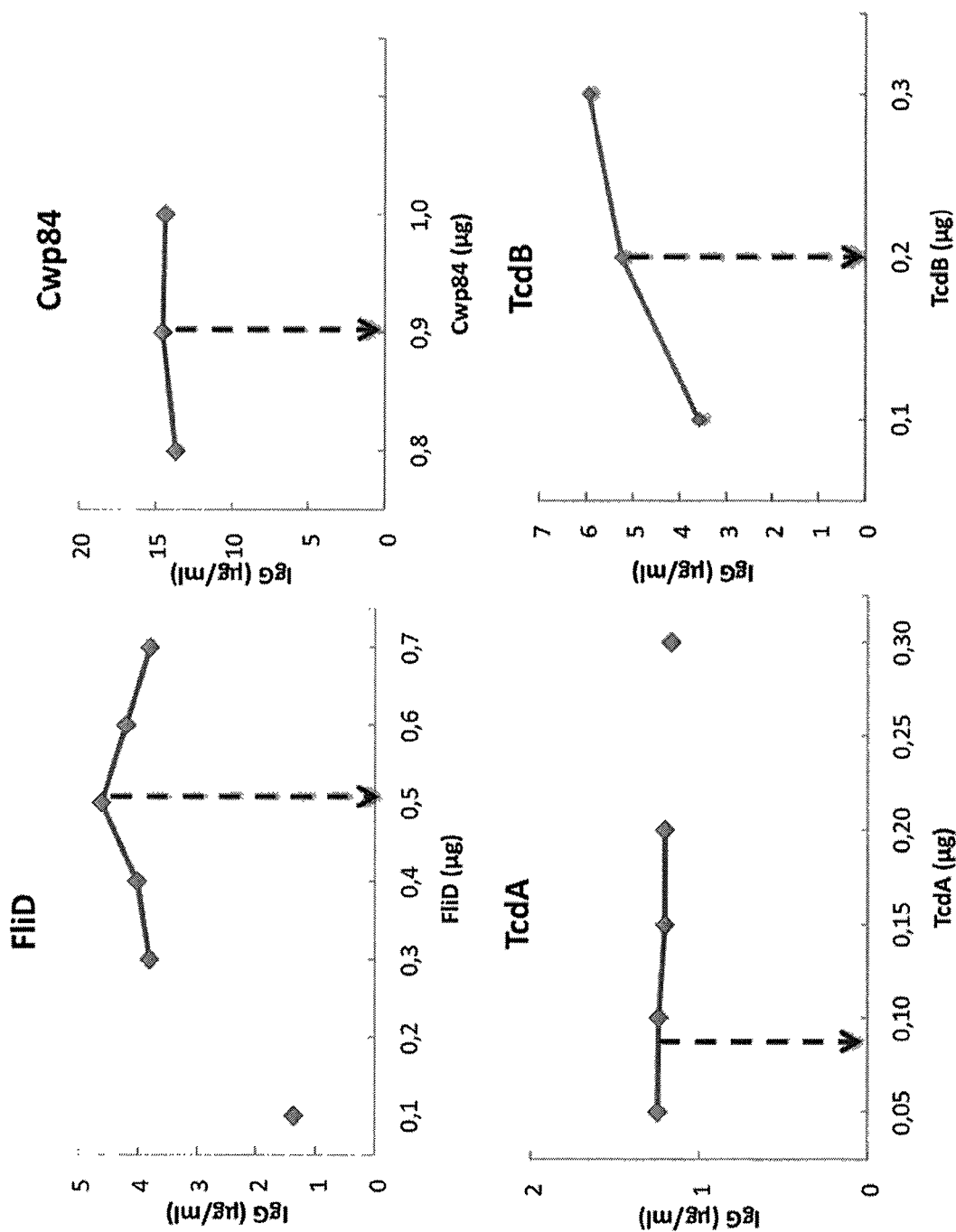
FIG. 4 depicts a graph for the optimal determination of antigens FliD, Cwp84, TcdA, TcdB concentration in the case of antibodies of the IgG isotype. The optimal concentrations of *C. difficile* antigens for coating of the wells have been chosen as allowing an optimal measure of antibody concentration, indicating antigen saturation of the wells. The optimal concentration of antigens is represented by the arrow.

2.2.1. Optimal Concentrations of FliD, Cwp84, TcdA, TcdB for the Coating of the Plates The optimal concentrations of *C. difficile* antigens for coating of the wells have been chosen as allowing an optimal measure of antibody concentration, indicating antigen saturation of the wells (FIG. 4, example for IgG isotype).

2.2.2. Standard Curves for the Calibrators

Figure 5:
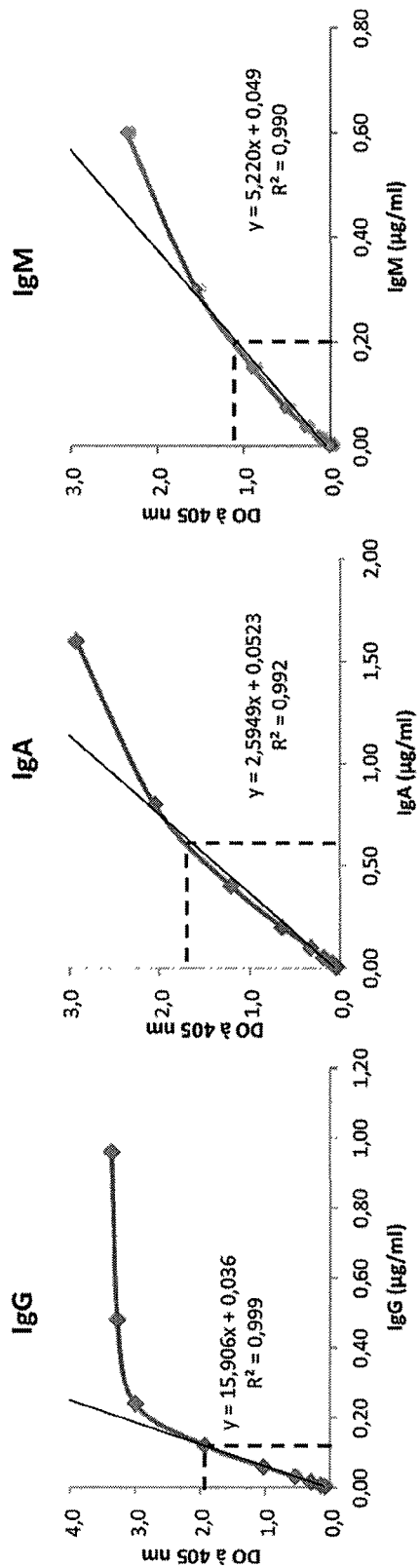
FIG. 5 depicts Standard curves obtained with solutions of purified polyclonal human IgG, IgA and IgM immunoglobulin for antibody quantification in sera.

OD/Ig standard curves for standard polyclonal human IgG, IgA and IgM immunoglobulin solutions of known concentrations were determined to quantify the level of antibodies in the various sera of the study subjects (FIG. 5).

Figure 6:
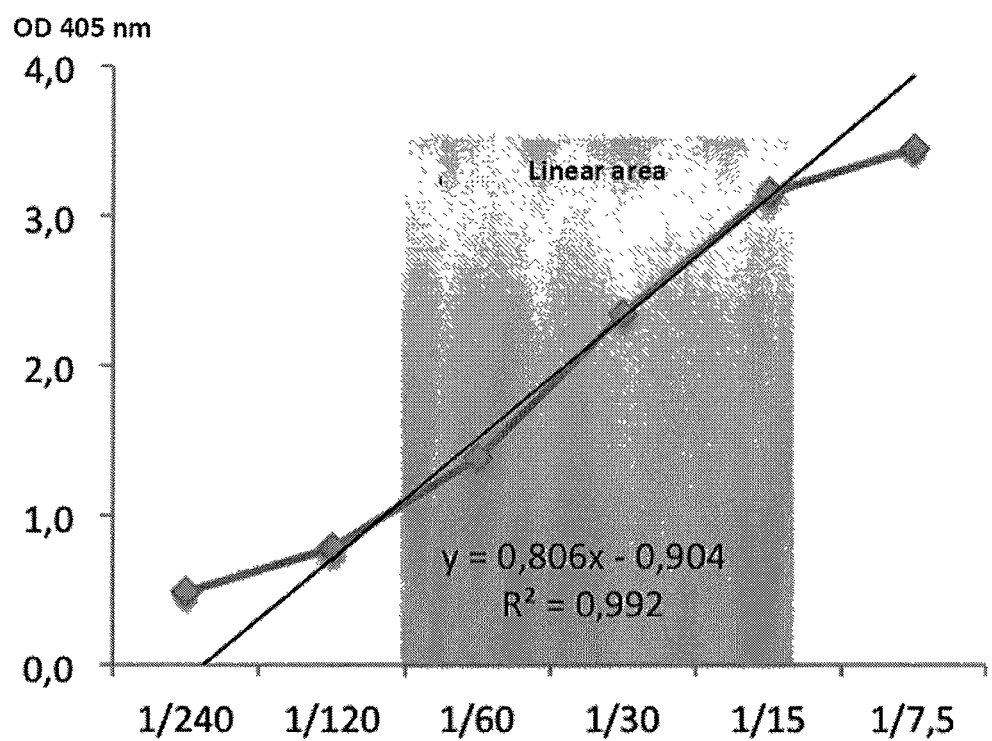
FIG. 6 depicts Determination of the linearity area for FliD-specific antibodies in the serum of a healthy volunteer exposed to *C. difficile*.

The linearity zone is determined as shown in FIG. 6.

The limits of quantification for each isotype are as follows: 0.066 µg/ml for IgG, 0.018 µg/ml for IgA and 0.014 µg/ml for IgM antibodies.

2.2.3. Interference in the ELISA Assay and Optimization

It is recognized that in all kinds of immunoassays the detection of the analytes can be influenced by interference. Very frequently cross reactivities, unspecific binding and matrix effects occur. Interfering substances are present in more or less significant concentrations in real specimen and interact with the analytes or with the capture respectively the detector antibodies directly [14].

Figure 7:
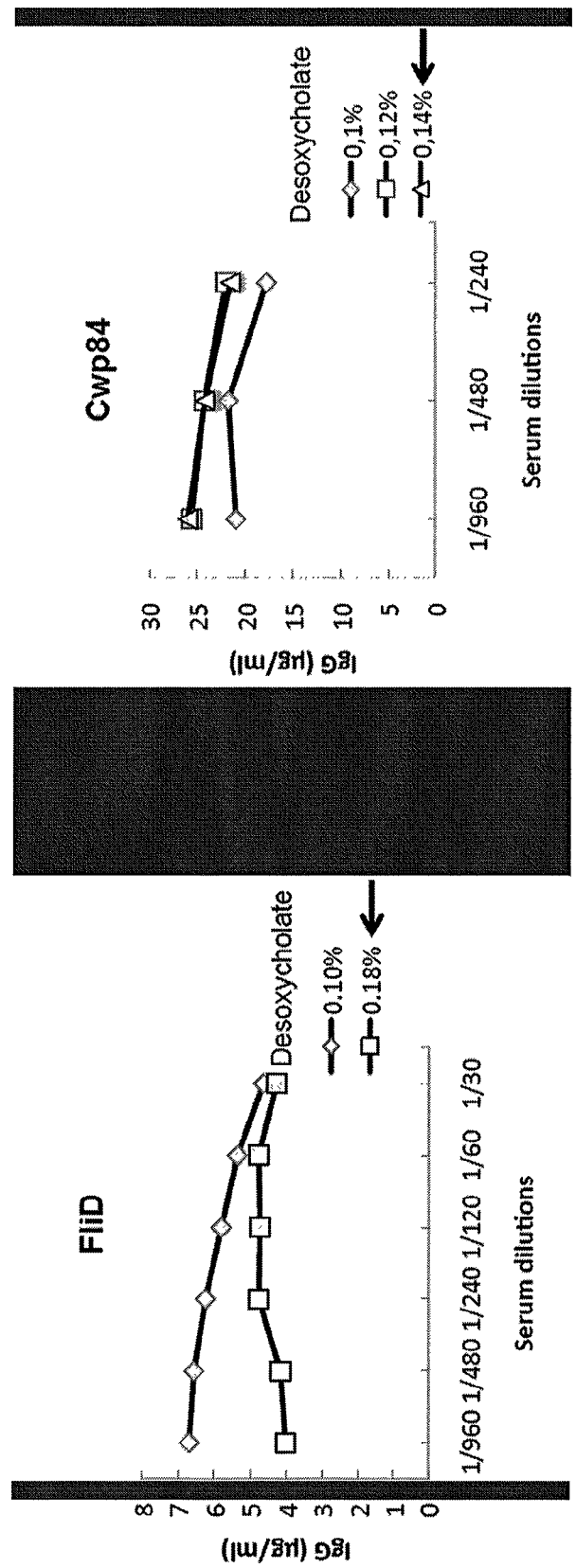
FIG. 7 depicts the impact on the interference of sodium deoxycholate concentration in the fixation buffer. It is an experiment on the interference detected when FliD- or Cwp84-specific IgG concentrations were measured in reference serums. FliD curves show that the proportionality between serum dilution and IgG concentration is not correct if the concentration of sodium deoxycholate is 0.1% in the coating buffer. However, increasing sodium deoxycholate concentration from 0.1% to 0.18% removes the interference. Therefore the latter concentration was chosen. Regarding Cwp84-specific IgG dosage, the interference was low, and 0.14% sodium deoxycholate was chosen.

FIG. 7 shows a representative experiment on the interference detected when FliD- or Cwp84-specific IgG concentrations were measured in reference serums. FliD curves show that the proportionality between serum dilution and IgG concentration is not correct if the concentration of sodium deoxycholate is 0.1% in the coating buffer. However, increasing sodium deoxycholate concentration from 0.1% to 0.18% removes the interference. Therefore the latter concentration was chosen. Regarding Cwp84-specific IgG dosage, the interference was low, and 0.14% sodium deoxycholate was chosen.

Figure 8:
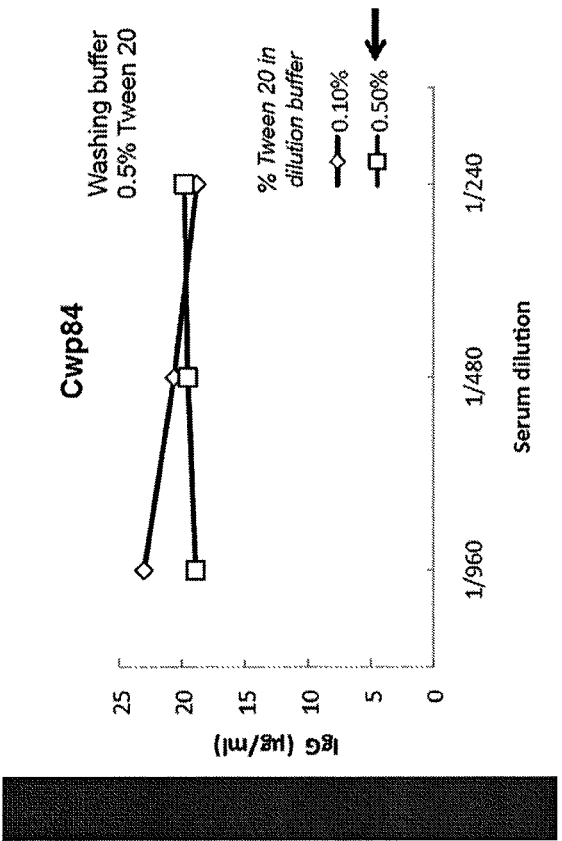
FIG. 8 depicts Impact on the interference of Tween®20 concentration in the washing buffer Optimization of the assay was obtained setting Tween 20® concentration at 0.1% and 0.5% for FliD- and Cwp84-antibody dosage respectively. Same approach was used for the dilution buffer.
Figure 8:
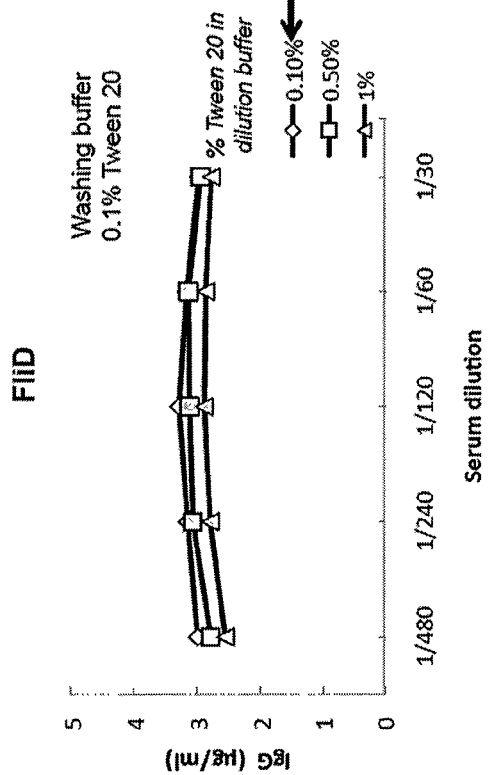

FIG. 8 shows that the concentration of Tween 20® in the washing buffer also impacts on the interference. Optimization of the assay was obtained setting Tween 20® concentration at 0.1% and 0.5% for FliD- and Cwp84-antibody dosage respectively. Same approach was used for the dilution buffer.

Table 1 summarizes the composition of the buffers allowing optimal conditions for the ELISA dosage of antibodies specific for *C. difficile* proteins.

2.2.4. Reproducibility of the ELISA Assay

Figure 9:
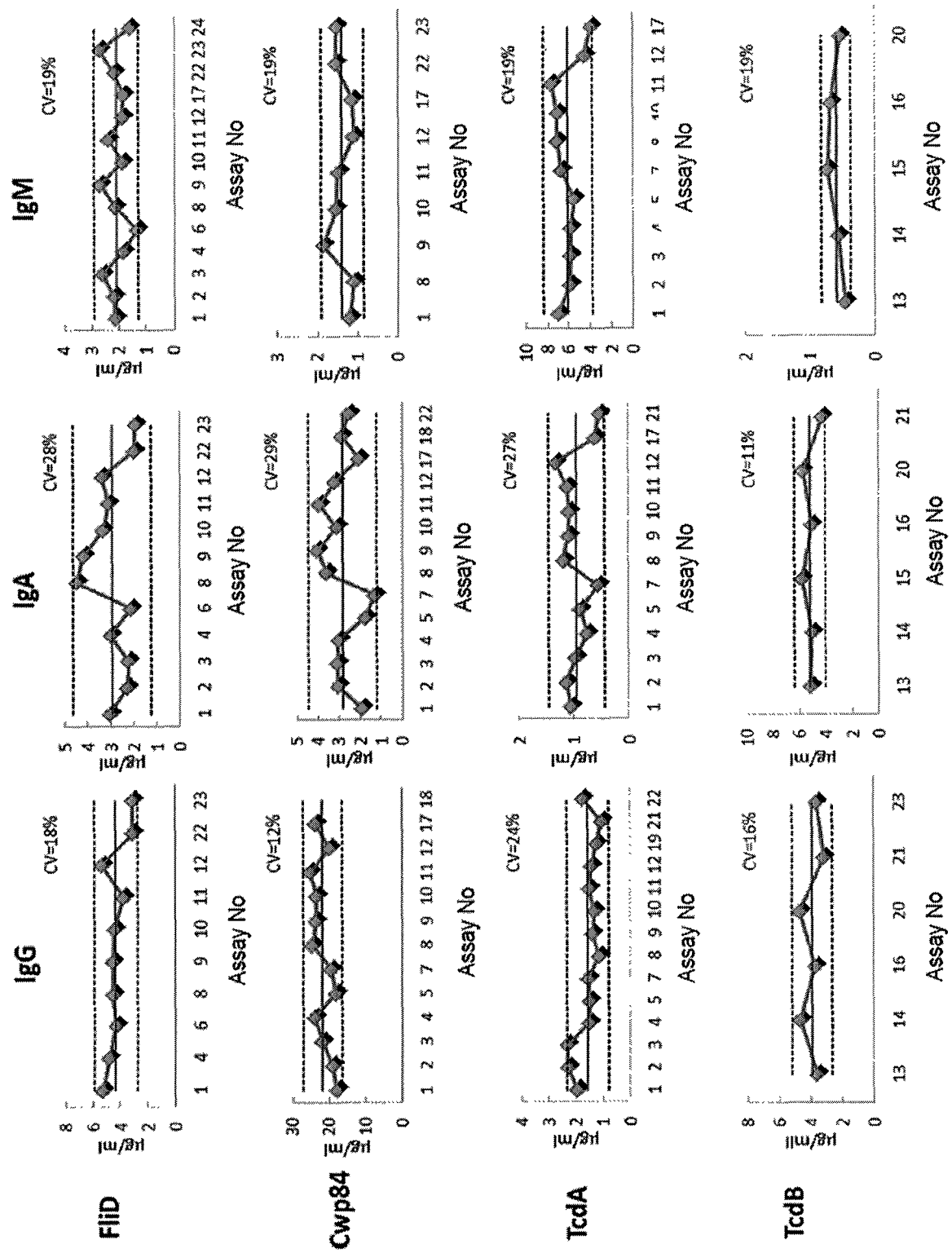
FIG. 9 depicts the reproducibility of the assay evaluated with the reference serum (IgG and IgM) and lactoserum (IgA) tested at least in five distinct experiments. The mean value is shown by the continuous line, and two standard deviations are shown in dotted lines.

The reproducibility of the assay was evaluated with the reference serum (IgG and IgM) and lactoserum (IgA) tested at least in five distinct experiments (blue line). The mean value is shown by the red line, and two standard deviations are shown in dotted lines (FIG. 9).

Figure 10:
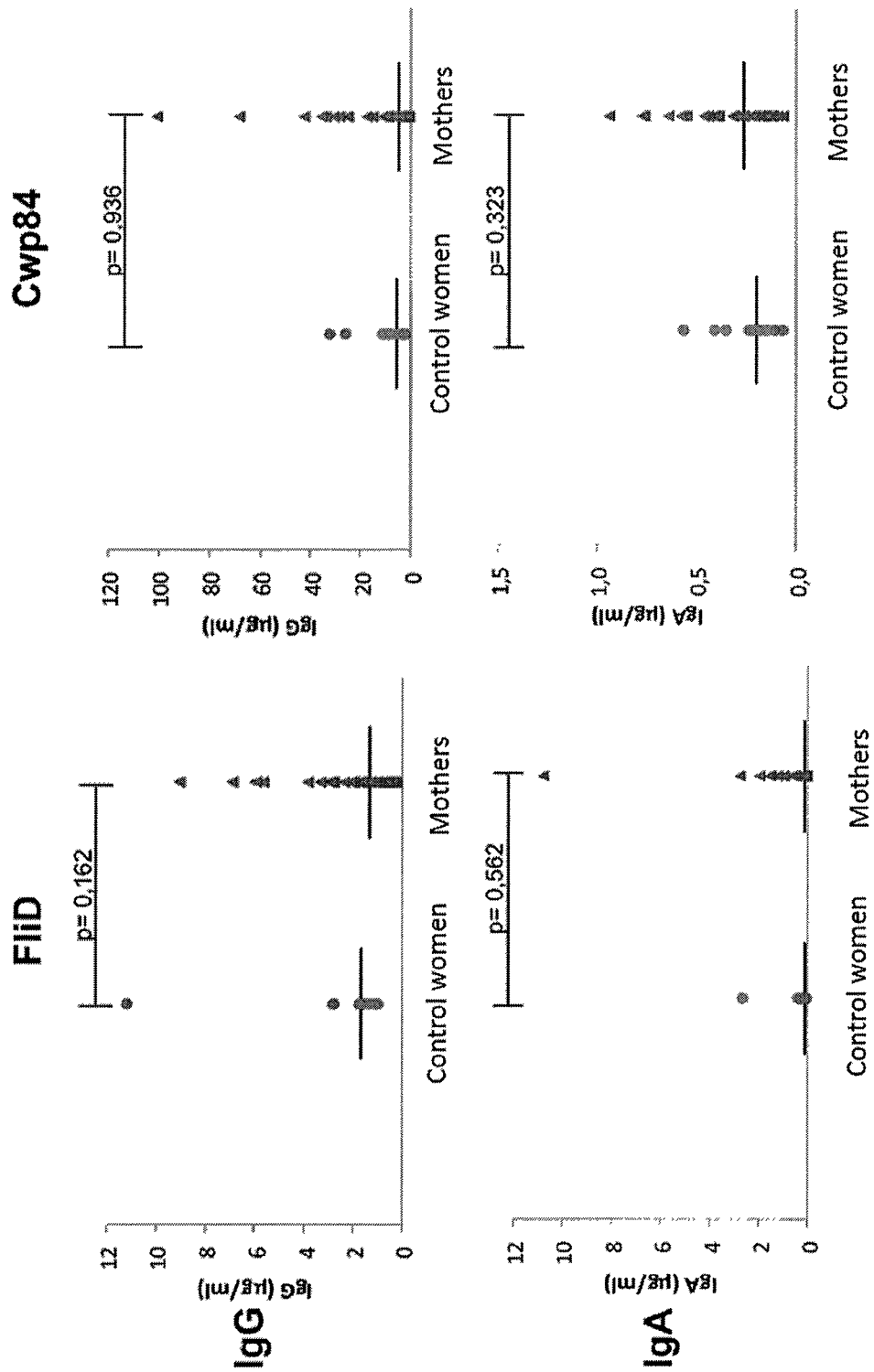
FIG. 10 depicts FliD- and Cwp84-specific IgG and IgA antibodies in serum from pregnant women (n=44) and age-matched control women (n=12). Each dot represents a single subject. Statistical comparison was performed with the Mann Whitney test.

2.3. Immunity Specific for *C. difficile* in Pregnant Women as Compared with Age-Matched Control Women The data in FIG. 10 show levels of IgG and IgA antibodies specific for *C. difficile* colonization factors FliD and Cwp84 in pregnant women vs age-matched control women. Substantial levels of IgG antibodies specific for these two factors were detected in both groups, with a great variability between subjects, and the levels of Cwp84-specific IgG were particularly elevated in some pregnant women, even reaching 101 µg/ml for one of them. As expected, serum IgA levels directed against these two molecules were quite low in the two groups. These data also shows that no significant differences were detected between the two groups, whatever the antigen or the isotype considered.

TABLE 2 median and range values for IgG, IgA and IgM against the 2 colonization factors.

|  |  | FliD | | Cwp84 | |
|---|---|---|---|---|---|
|  |  | Controls (12) | Mothers (44) | Controls (12) | Mothers (44) |
| IgG | Median (µg/ml) | 1.328 | 1.690 | 5.376 | 4.768 |
|  | Range (min-max) | 1.002-11.199 | 0.262-9.082 | 1.728-32.65 | 0.530-100.925 |
| IgA | Median (µg/ml) | 0.092 | 0.134 | 0.200 | 0.260 |
|  | Range (min-max) | <0.066-2.65 | <0.066-10.775 | <0.066-0.564 | <0.066-0.938 |
| IgM | Median (µg/ml) | 1.569 | 0.538 | 0.716 | 0.354 |
|  | Range (min-max) | 0.308-3.462 | 0.106-5.896 | 0.389-1.773 | 0.081-3.155 |

Figure 11:
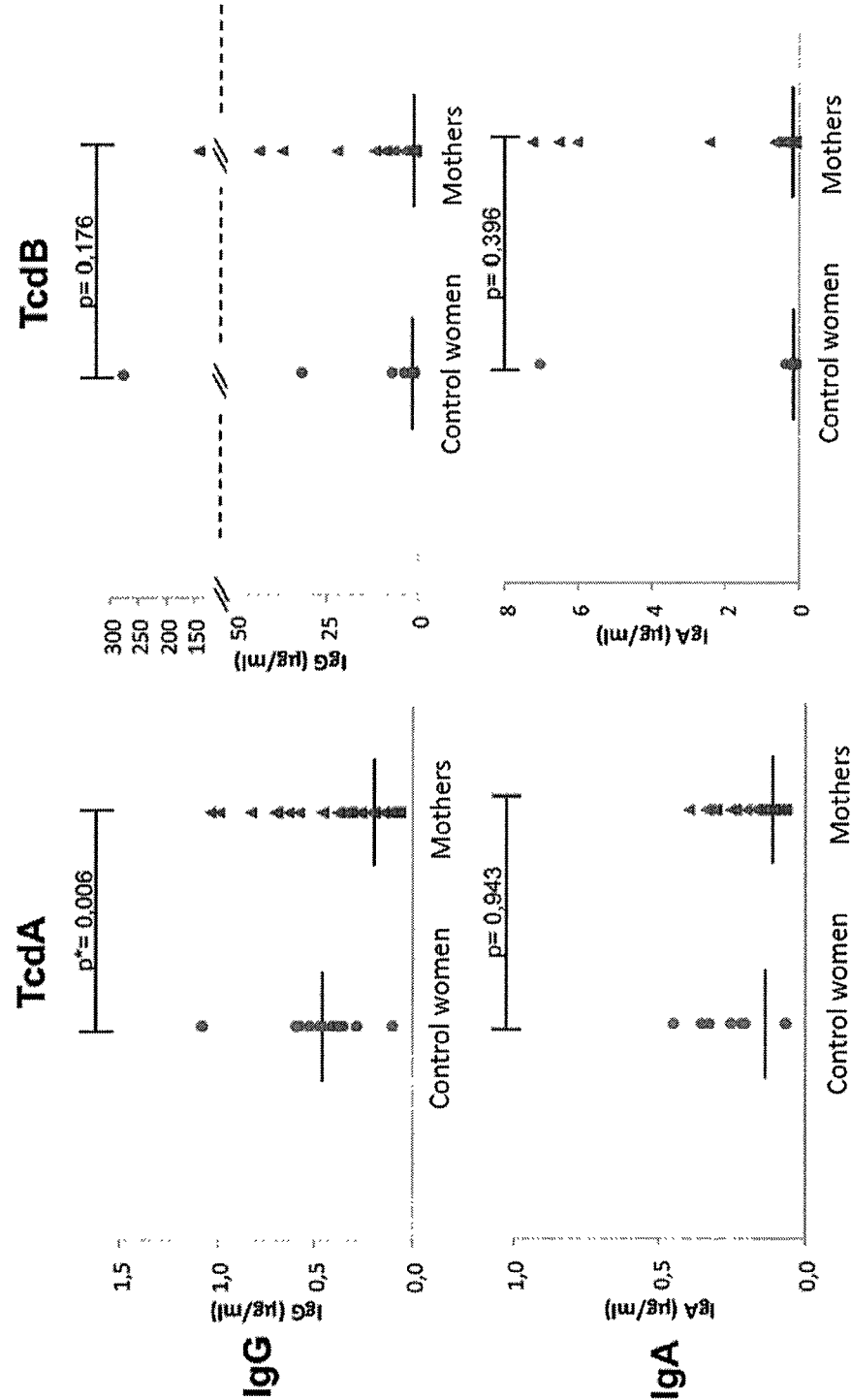
FIG. 11 depicts TcdA and TcdB-specific IgG and IgA antibodies in serum from pregnant women (n=44) and age-matched control women (n=12). Each dot represents a single subject. Statistical comparisons were performed with the Mann Whitney test. The same variability between subjects was noticed, some of the mothers showing very high concentrations of TcdB-specific IgG, even reaching 141 µg/ml in one of them. As observed for the response to the colonizing factors, no significant differences were detected between the two groups at the IgA level, and for TcdB-specific IgG, while a significant reduction in TcdA-specific IgG response was observed in the pregnant women group. The reason for this difference is unclear, but the comparison between the two groups may be biased by the great variability of the response within a group and the imbalance in the number of subjects per group (n=44 vs n=12).

FIG. 11 shows levels of IgG and IgA antibodies specific for the two toxins of *C. difficile*, TcdA and TcdB in the two groups of subjects. The same variability between subjects was noticed, some of the mothers showing very high concentrations of TcdB-specific IgG, even reaching 141 µg/ml in one of them. As observed for the response to the colonizing factors, no significant differences were detected between the two groups at the IgA level, and for TcdB-specific IgG, while a significant reduction in TcdA-specific IgG response was observed in the pregnant women group. The reason for this difference is unclear, but the comparison between the two groups may be biased by the great variability of the response within a group and the imbalance in the number of subjects per group (n=44 vs n=12).

It is noteworthy that the two mothers who showed high levels of Cwp84-IgG or TcdB-IgG were *C. difficile* carriers.

Table 3 gives the median and range values of the IgG, IgA, and IgM response to TcdA and TcdB.

| | Detergent (%) | | | |
|---|---|---|---|---|
| Buffer | FliD | Cwp84 | TcdA | TcdB |
| Fixation Buffer | Deoxycholate 0.18% | Deoxycholate 0.14% | Deoxycholate 0.14% | Deoxycholate 0.14% |
| Washing Buffer | Tween ®20 0.1% | Tween ®20 ® 0.5% | Tween ®20 0.1% | Tween ®20 0.1% |
| Dilution Buffer | Tween ®20 0.1% for all isotypes | IgG: Tween ®20 0.5% IgA: Tween ®20 0.1% IgM: Tween ®20 0.5% | Tween ®20 0.1% for all isotypes | Tween ®20 0.1% for all isotypes |

TABLE 3

Median and range values for IgG, IgA and IgM response against the 2 C. difficile toxins

|     |                  | TcdA          |               | TcdB          |               |
|-----|------------------|---------------|---------------|---------------|---------------|
|     |                  | Controls (12) | Mothers (44)  | Controls (12) | Mothers (44)  |
| IgG | Median (µg/ml)   | 0.462         | 0.199         | 1.558         | 1.208         |
|     | Range (min-max)  | 0.102-1.079   | 0.062-1.038   | 0.881-278.772 | 0.508-141.44  |
| IgA | Median (µg/ml)   | 0.136         | 0.111         | 0.163         | 0.185         |
|     | Range (min-max)  | <0.066-0.451  | <0.066-0.398  | <0.066-7.056  | <0.066-6.54   |
| IgM | Median (µg/ml)   | 0.431         | 0.135         | 0.204         | 0.217         |
|     | Range (min-max)  | 0.177-0.960   | 0.042-0.758   | 0.061-0.572   | 0.042-0.960   |

Figure 12:
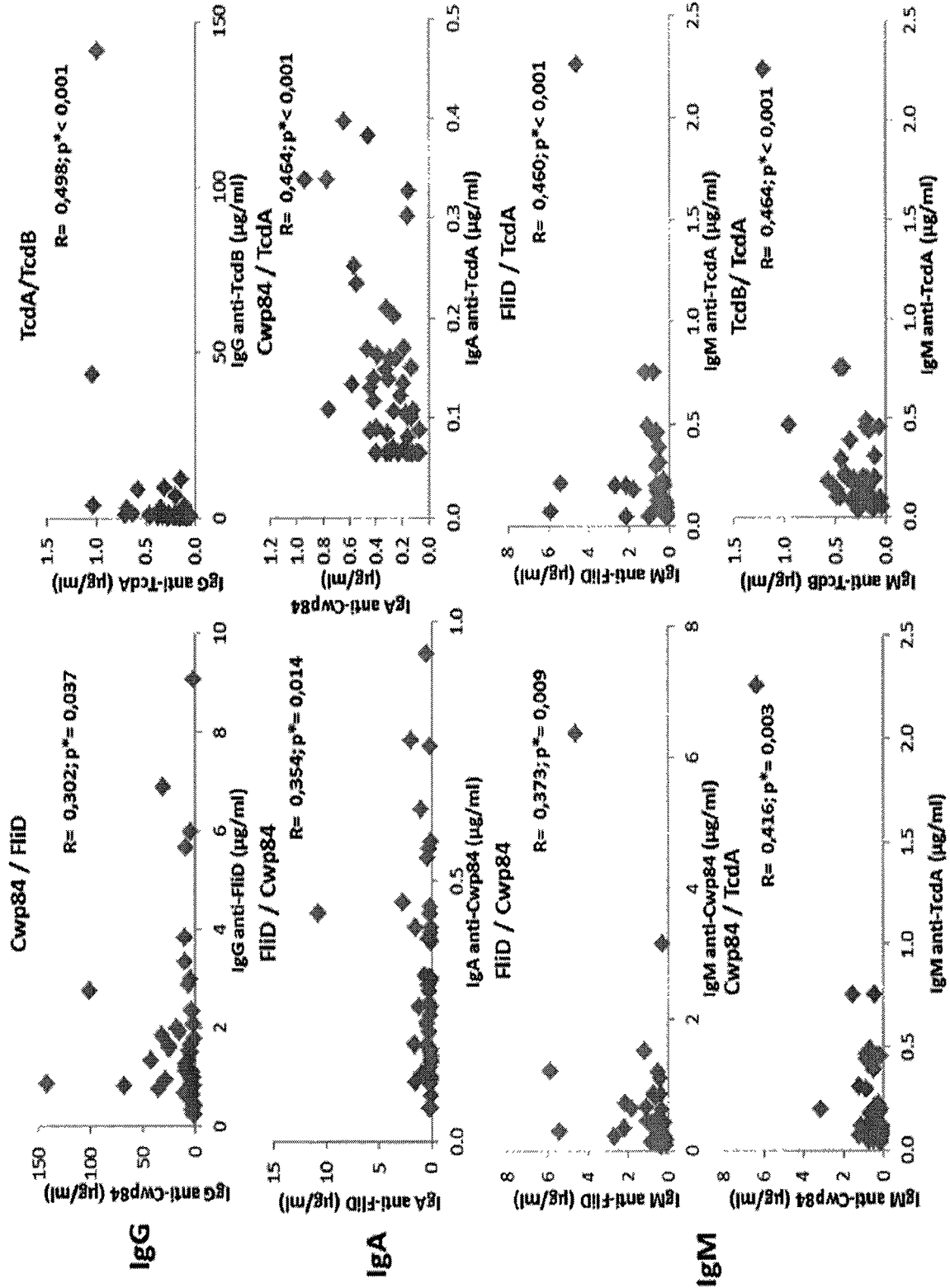
FIG. 12 depicts correlations between Cwp84, FliD, TcdA and TcdB IgG, IgA and IgM levels in serum from pregnant women Spearman correlations between serum IgG, IgA and IgM levels specific for the four antigens are shown. The correlation coefficient R and p values are indicated. $P<0.05$ was considered as significant.

Overall, these data show that the sera from all the women tested contain IgG and IgM antibodies against the two colonization factors, FliD and Cwp84, but the levels of these antibodies was highly variable within the groups tested. Regarding the levels of antibodies specific for the toxins, the same variability was observed between subjects and the levels were quite low, except for IgG anti-TcdB. As expected, IgA levels against the 4 antigens were lower in sera. The high seroprevalence specific for *C. difficile* in healthy adults and the substantial levels of IgG specific for the 4 molecules tested are in favor of an exposure to *C. difficile* (environmental exposure during early infancy and perpetuated through adult life), as previously suggested [8] [15]. FIG. 12 shows the Spearman correlations between these responses.

2.4. Detection of IgG, IgA and IgM Specific for FliD and Cwp84 in Cord Blood and Lactoserum.

Figure 13:
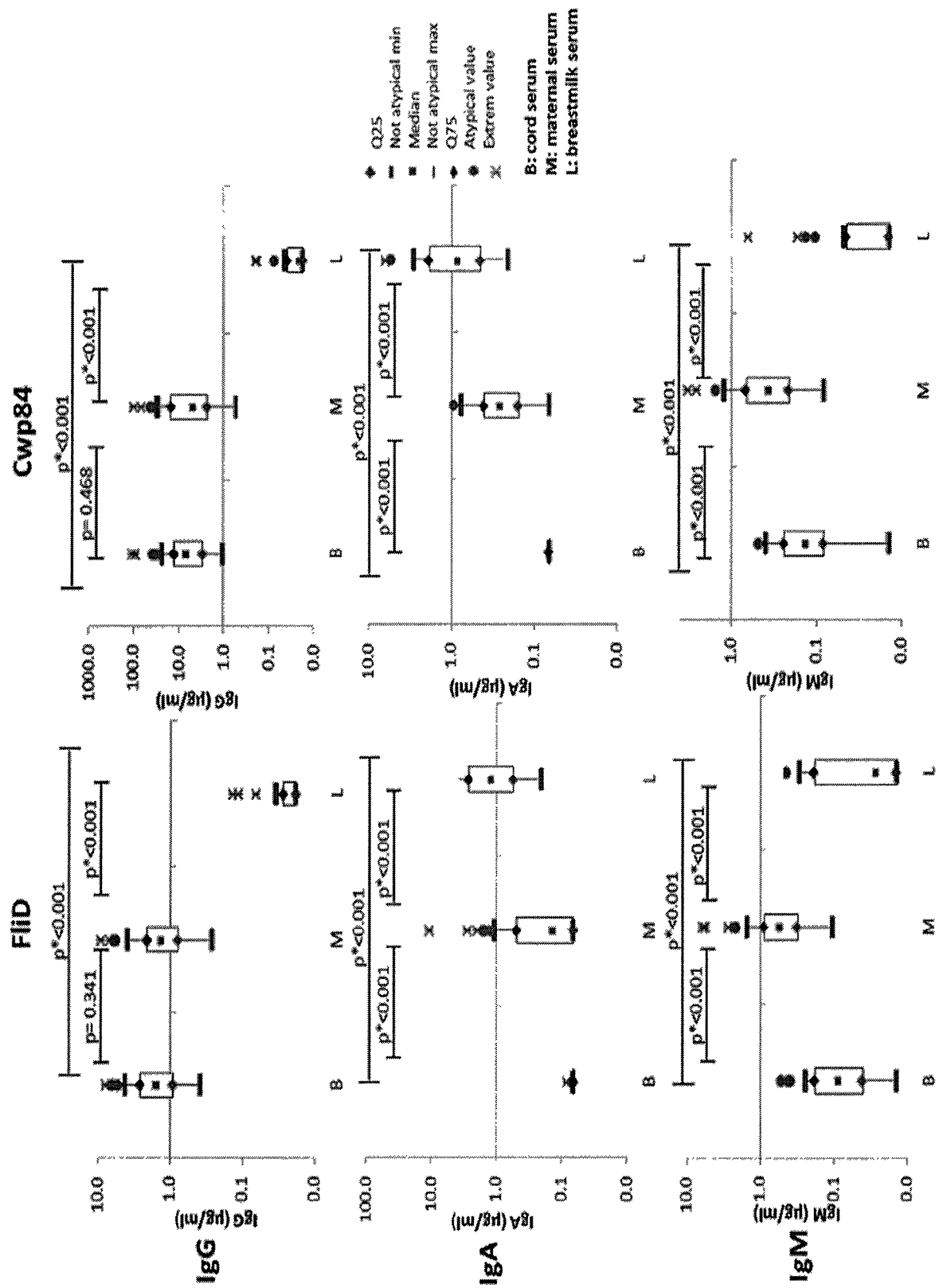
FIG. 13 depicts FliD and Cwp84 antibody levels in cord serum and breast milk IgG, IgA and IgM antibody levels specific for FliD and Cwp84 in cord blood serum (B) (n=44), maternal serum (M) (n=44) and breast milk serum (L) (n=18). Box plots show the median value, minimum, maximum and extreme values. Statistical comparisons were performed with the Mann Whitney test. $P<0.05$ was considered as significant.

The ELISA assay has been used to detect *C. difficile* specific antibodies in cord blood and lactoserum. Data in FIG. 13 show the median values of antibodies specific for the 2 colonization factors in cord blood (n=44), mothers' serum (n=44) and lactoserum (n=18). There was no significant differences in the levels of IgG specific for the 2 antigens in cord blood vs mothers' serum, in contrast to IgG levels in lactoserum that were much lower compared to cord blood and mothers' serum. As expected, specific-IgA levels were significantly much higher in lactoserum compared to mothers' serum and undetectable in cord blood. IgM levels were low to undetectable in cord blood and lactoserum. Thus, lactoserum is enriched in IgA specific for FliD and Cwp84, while cord blood contains almost exclusively IgG specific for these 2 colonization factors.

2.5. Detection of IgG, IgA and IgM Specific for TcdA and TcdB in Cord Blood and Lactoserum.

Figure 14:
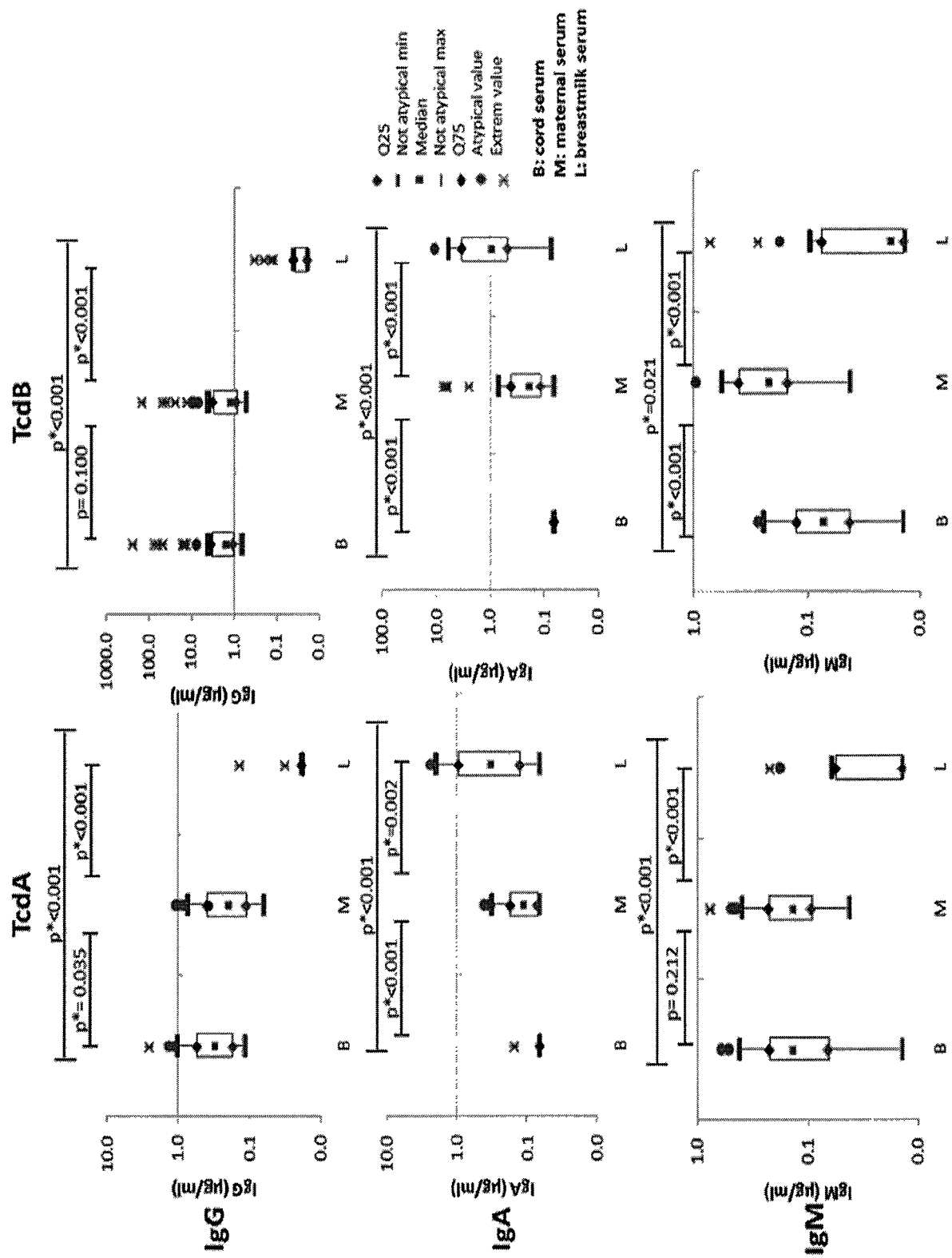
FIG. 14 depicts TcdA and TcdB antibody levels in cord serum and breast milk IgG, IgA and IgM antibody levels specific for TcdA and TcdB in cord serum (B) (n=44), maternal serum (M) (n=44) and breast milk serum (L) (n=18). Box plots show the median value, minimum, maximum and extreme values. Statistical comparisons were performed with the Mann Whitney test. P<0.05 was considered as significant.

FIG. 14 shows the median values of antibodies specific for the TcdA and TcdB in cord blood (n=44), mothers' serum (n=44) and lactoserum (n=18). The antibody patterns were quite similar to those reported above for the colonization factors, characterized by same range levels of IgG in cord blood vs mothers' serum, very low IgG directed to these toxins in lactoserum, and specific-IgA levels significantly higher in lactoserum compared to mothers' serum and cord blood. Thus, lactoserum is enriched in IgA specific for TcdA and TcdB, while cord blood contains almost exclusively IgG specific for these 2 toxins.

2.6. Mother to Child Transmission of *C. difficile*-Specific IgG Antibodies

With the aim to address the question of mother to child transmission of *C. difficile*-specific antibodies, spearman correlations were performed for IgG antibodies to compare the levels of cord blood to mothers' IgG antibodies. Very strong correlations were found for the IgG levels specific for the 4 *C. difficile* antigens, the correlation coefficient being >0.9, strongly arguing for a mother to child transmission (FIG. 15).

2.7. Positive Correlation Between *C. difficile*-Specific Antibody Levels in Lactoserum and Blood.

Figure 16:
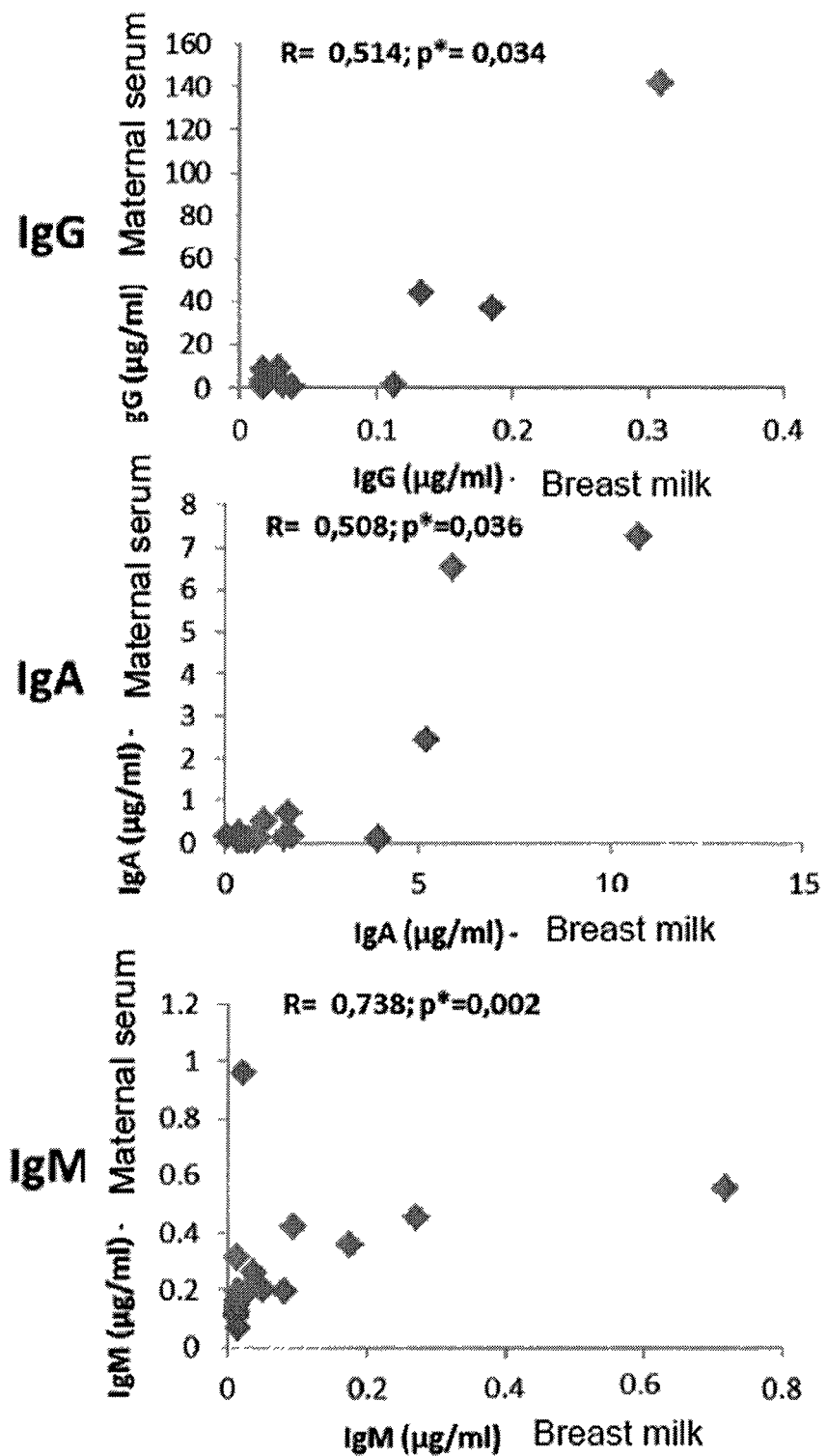
FIG. 16 depicts Correlations between maternal serum and breast milk TcdB-specific IgG, IgA and IgM Spearman correlations between maternal serum and breast milk (n=18) IgG, IgA and IgM levels specific for TcdB are shown. The correlation coefficient R and p values are indicated on each panel. P<0.05 was considered as significant.

FIG. 16 shows Spearman correlations between TcdB-specific IgG, IgA and IgM levels in lactoserum and blood serum from the mothers. A positive correlation was detected for the three isotypes, as expected.

Figure 15:
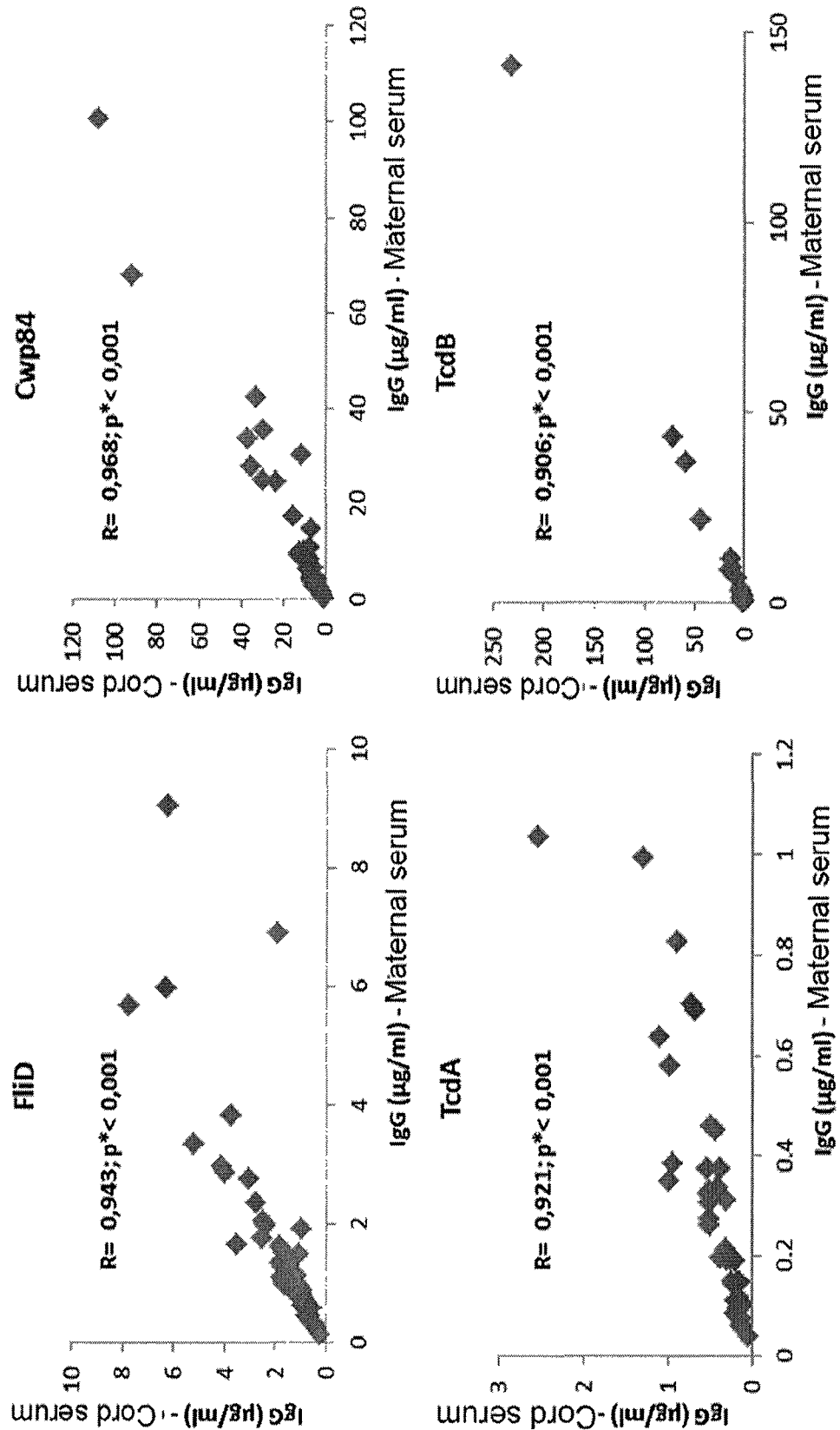
FIG. 15 depicts Correlations between maternal serum and cord serum IgG levels specific for FliD, Cwp84, TcdA and TcdB Spearman correlations between maternal serum and cord serum (n=44) IgG specific for *C. difficile* antigens are shown. The correlation coefficient R and p values are indicated. P<0.05 was considered as significant.

Overall, data from FIGS. 15 and 16 highlight the mechanisms of immune protection of neonates by mother to child transmission of antibodies via both the placenta and breast milk.

2.8. Humoral Immunity of Colonized Mothers and their Newborn

Among the cohort of paired mothers/newborn that we studied, three of them (M22-M24) were found colonized with non-toxinogenic *C. difficile*. Table 4 compares their humoral immunity to that of non-carrier mothers and non-carrier neonates. It shows that the IgM response to the colonization factors FliD and Cwp84 of the infected mothers was stronger compared to that of non-carrier mothers while the IgG response was lower. This pattern is evocative of a specific primary response to this colonisation.

TABLE 4

Comparative humoral immunity of mother/neonates carriers of C. difficile with that of non-carriers mothers and neonates The low IgM and IgG response to TcdA and TcdB was expected since the strains of C. difficile isolated were non toxigenic.

|          | C. difficile | IgM (µg/ml) |       |      |      | IgG (µg/ml) |       |      |       |
|----------|--------------|-------------|-------|------|------|-------------|-------|------|-------|
| Patients | in stools    | FliD        | Cwp84 | TcdA | TcdB | FliD        | Cwp84 | TcdA | TcdB  |
| M22      | NT           | 1.21        | 0.73  | 0.25 | 0.20 | 0.57        | 1.45  | 0.83 | 1.765 |
| B22      | +            | 0.09        | 0.25  | 0.22 | 0.05 | 0.66        | 2.10  | 0.89 | 2.23  |
| M23      | −            | 5.90        | 1.22  | 0.08 | 0.12 | 0.44        | 0.53  | 0.28 | 0.508 |
| B23      | +            | 0.08        | 0.13  | 0.19 | 0.05 | 0.71        | 1.03  | 0.50 | 0.93  |
| M24      | +            | 2.15        | 0.73  | 0.05 | 0.12 | 0.65        | 2.96  | 0.31 | 9.39  |

TABLE 4-continued

Comparative humoral immunity of mother/neonates carriers of C. difficile
with that of non-carriers mothers and neonates The low IgM and IgG
response to TcdA and TcdB was expected since the strains of
C. difficile isolated were non toxigenic.

| Patients | C. difficile in stools | IgM (µg/ml) | | | | IgG (µg/ml) | | | |
|---|---|---|---|---|---|---|---|---|---|
| | | FliD | Cwp84 | TcdA | TcdB | FliD | Cwp84 | TcdA | TcdB |
| B24 | − | 0.08 | 0.12 | 0.12 | 0.05 | 0.92 | 5.38 | 0.51 | 12.24 |
| Non-carrier mothers (n = 38) | − | | | | | | | | |
| Median | | 0.50 | 0.34 | 0.14 | 0.20 | 1.22 | 5.62 | 0.20 | 1.15 |
| Range (min-max) | | 0.11-5.90 | 0.09-3.16 | 0.04-0.76 | 0.04-0.96 | 0.26-9.08 | 0.53-67.95 | 0.06-1.04 | 0.51-43.87 |
| Non-carrier neonates (n = 33) | − | | | | | | | | |
| Median | | 0.07 | 0.12 | 0.12 | 0.08 | 1.71 | 6.67 | 0.32 | 1.48 |
| Range (min-max) | | <0.014-0.52 | 0.03-0.47 | <0.014-0.61 | <0.014-0.24 | 0.37-7.28 | 1.13-108.9 | 0.12-2.54 | 0.65-231.9 |

NT: not tested.

2.9. Longitudinal Analysis of C. difficile-Specific Immunity in Infected Symptomatic Women, and Impact on Recurrence of the Infection.

Twelve pregnant women who developed C. difficile infection during antepartum (n=7) or perpartum or early postpartum periods (n=5) were included in the study. 15% (2/12) of them developed a severe form of the disease, including pseudomembranous colitis (Pt 4), toxic megacolon, and 15% (2:12) experimented recurrent CDI (Pt 3). 83% (10/12) of them received antibiotics treatment prior to the infection, and C. difficile infection was nosocomial in 75% (9/12) of these women.

Figure 17:
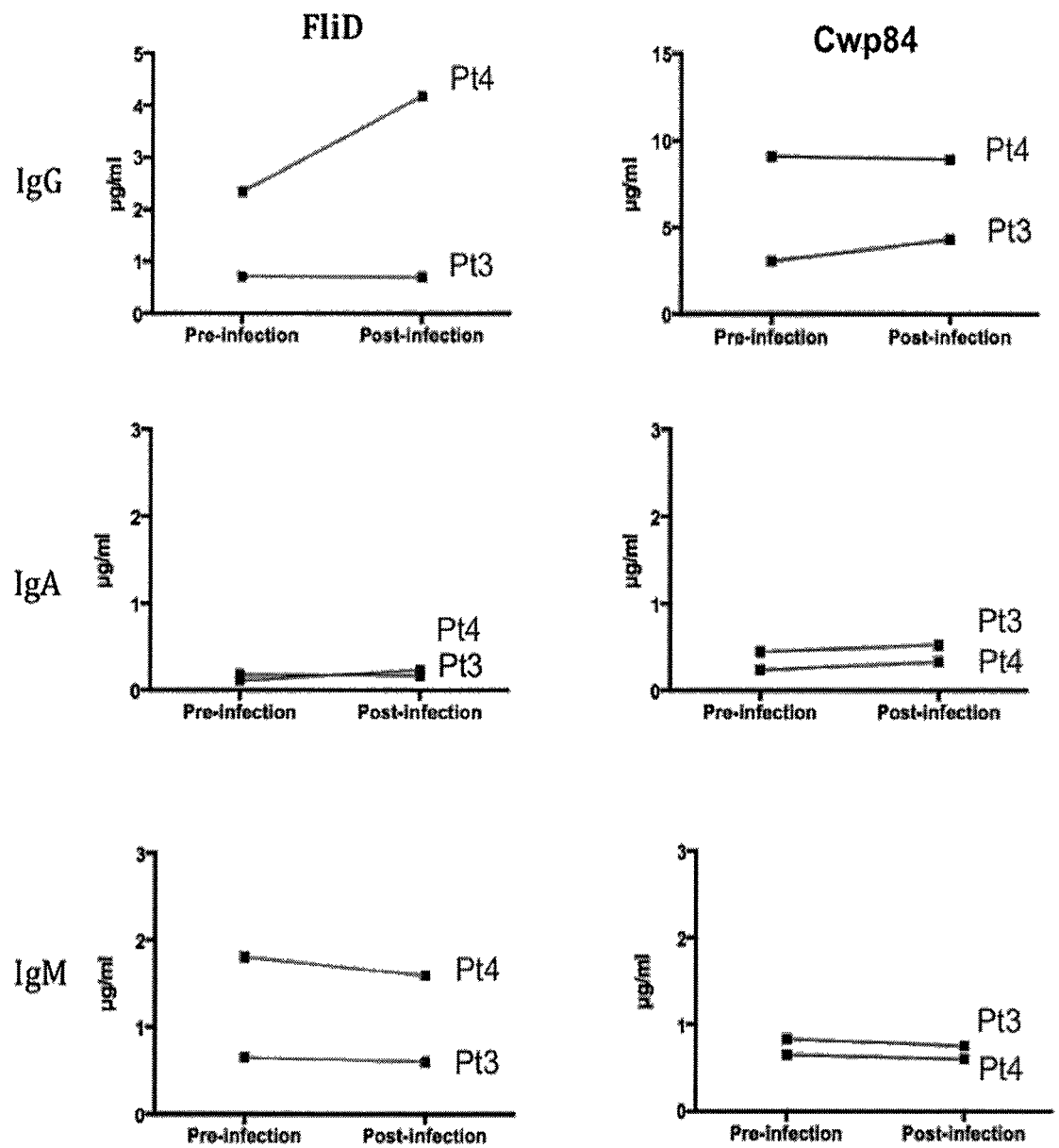
FIG. 17 depicts Comparison of FliD- and Cwp84-specific antibodies pre- and post-infection in recurrent vs non-recurrent infection FliD- and Cwp84-specific IgG, IgA and IgM antibody pattern in Patient 3 (Pt3), who showed recurrent *C. difficile* infections and Patient 4 (Pt 4), who did not show any recurrence.
Figure 18:
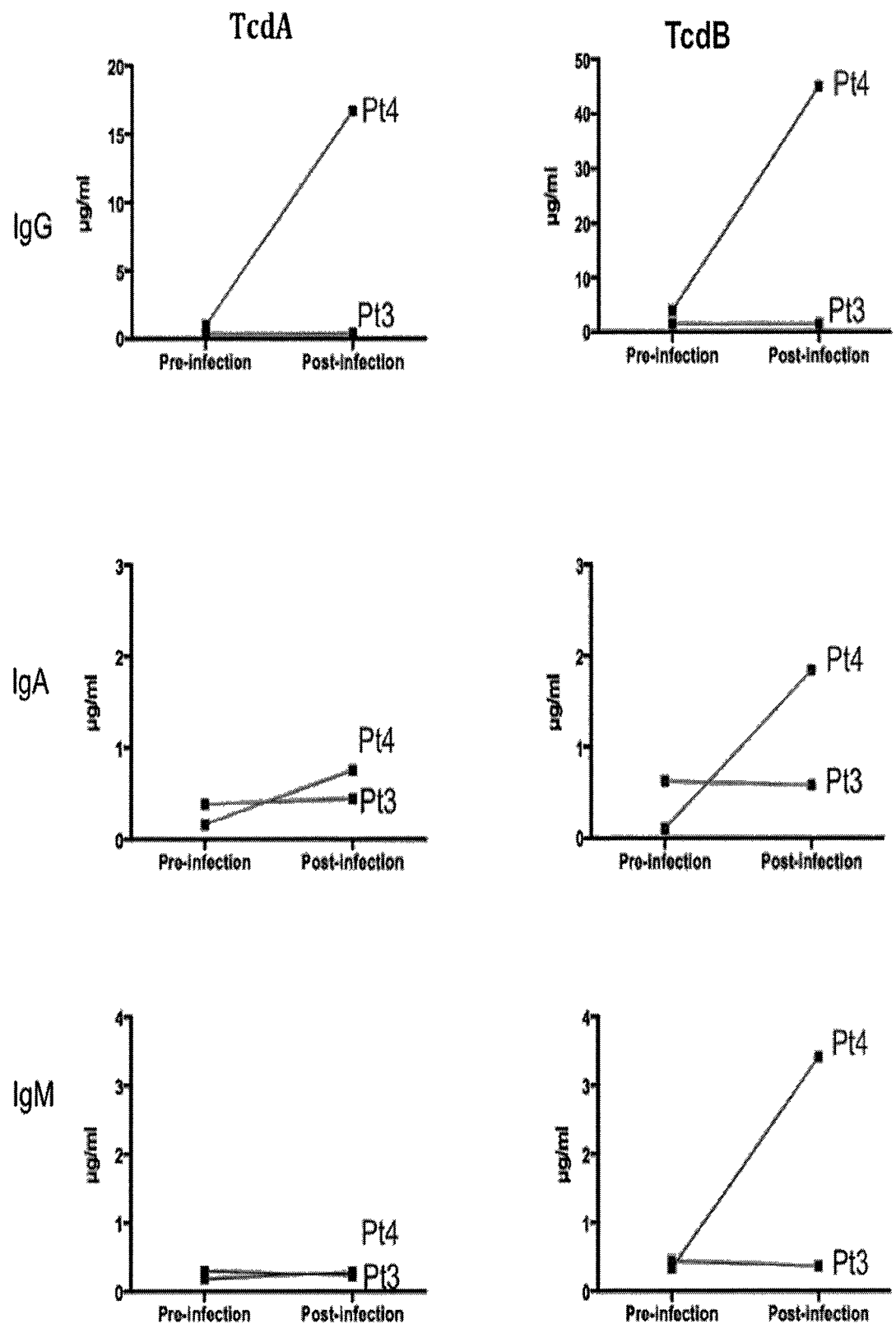
FIG. 18 depicts Comparison of TcdA- and TcdB-specific antibodies pre- and post-infection in recurrent vs non-recurrent infection TcdA- and TcdB-specific IgG, IgA and IgM antibody pattern in Patient 3 (Pt3), who showed recurrent *C. difficile* infections and Patient 4 (Pt 4), who did not show any recurrence.

For five of these patients, both pre-infection and post-infection sera were available, and FIGS. 17 and 18 compare the antibody pattern specific for the four C. difficile proteins in Pt 4, who did not show any recurrence, versus Pt 3, who showed recurrent infections.

Pt 3: pre-infection serum obtained at day −21 before the infection (infection being day 0), and post-infection serum obtained at day +31 after the infection from Pt3 patient; Pt 4: pre-infection serum obtained at day −159 before the infection, and post-infection serum obtained at day +12 after the infection from Pt4 patient.

We observed that, in all the patients except one (Pt 4), antibody levels specific for FliD, TcdA and TcdB were low before infection and they were not increased following infection with C. difficile (summarized in Table 5). In contrast, Patient 4 developed a strong IgG response against FliD, TcdA and TcdB, and the level of IgM antibodies specific for FliD was high before infection (FIG. 17). This antibody pattern was associated with the absence of recurrence in this patient. In contrast, recurrent infection occurred in Pt 3 who did not mount an antibody response either against the colonization factors or against the toxins.

These observations extend to a larger panel of antigens the initial report by Kyne et al. of the association between IgG antibody response to toxin A and protection against recurrent C. difficile diarrhoea. In particular, we report that protection against recurrence in Pt 4 is also associated with strong IgG to FliD, TcdA and TcdB (Table 5).

The potential protective effect of TcdB-specific IgG is in agreement with the observation that TcdB is essential for virulence of C difficile [16].

TABLE 5

Comparison of the antibody response in the infected and protected patient
4 to the antibody response of non-responder (NR) infected patient.

| | | FliD | Cwp84 | TcdA | TcdB |
|---|---|---|---|---|---|
| IgG (µg/ml) | Patient 4 | 2.35 | 3.06 | 1.03 | 4.03 |
| | Median NR patients | 0.88 | 9.12 | 0.15 | 1.40 |
| | Range (min-max) | 0.71-1.86 | 0.53-141.84 | 0.05-0.38 | 0.71-1.56 |
| IgA (µg/ml) | Patient 4 | 0.11 | 0.24 | 0.16 | 0.10 |
| | Median NR patients | 0.20 | 0.30 | 0.11 | 0.29 |
| | Range (min-max) | <0.066-1.62 | <0.066-0.45 | 0.09-0.38 | 0.17-0.62 |
| IgM (µg/ml) | Patient 4 | 1.80 | 0.65 | 0.18 | 0.33 |
| | Median NR patients | 0.46 | 0.44 | 0.12 | 0.18 |
| | Range (min-max) | 0.04-0.65 | 0.11-1.12 | 0.08-0.30 | 0.07-0.44 |

3. Conclusions

In this study we reported the following findings:

This study is the first one to analyze in a quantitative way the humoral response to a panel of antigens specific for C. difficile in non-infected, asymptomatic carriers and infected patients.

We report and validate a quantitative ELISA assay assessing the concentrations of IgM-, IgG- and IgA-specific for the colonization factors FliD and Cwp84, and the toxins TcdA and TcdB of C. difficile in blood serum, cord serum and lactoserum (FIGS. 4 to 9, Table 1).

Due to its higher sensitivity compared to non-quantitative ELISA assays used in studies reported in the literature, our assay revealed that C. difficile seroprevalence against these 4 molecules is 100% in the adult population studied (FIGS. 10 and 11, Tables 2 and 3). This is higher than the prevalence reported by Viscidi et al. i.e. antibodies to toxin A present in 64% of subjects more than two years old and antibodies to toxin B present in 66% of subjects more than six months old [17].

The strong correlations we detected between the antibody responses against the *C. difficile* antigens and for the 3 isotypes IgM, IgG and IgA (FIG. 12) indicate that the four antigens FliD, Cwp84, TcdA and TcdB can be used as markers of the immune response directed to *C. difficile*.

With this assay, we show for the first time the detection of *C. difficile*-specific IgA in the lactoserum (FIGS. 13 and 14). Their reactivity towards the colonization factors FliD and Cwp84 should be protective against colonization in breast-feed neonates, as suggested by studies with other pathogens [18].

We also demonstrate the transfer to neonates of maternal immunity to *C. difficile* through passive acquisition of specific antibodies to newborns, IgG via placental transfer and IgA via breast-feeding (FIGS. 13 to 16). Given the high rate (~70%) of *C. difficile* colonization in infants <1 year of age without symptoms [15] [19] our findings argue for a materno-foetal protection.

Characterization of *C. difficile* immunity against the panel of antigens in symptomatic infected patients revealed that disease onset was associated with: 1—A very low level of *C. difficile* IgM and IgG antibodies before infection; 2—No induction of antibody response after infection in some cases (FIGS. 17, 18).

High IgM and IgG response to FliD before infection and strong induction of IgG response against FliD, TcdA and TcdB after infection are predictive of the absence of recurrence (FIGS. 17, 18, Table 5).

BIBLIOGRAPHIC REFERENCES

1. Valiente E, Dawson L F, Cairns M D, Stabler R A, Wren B W: Emergence of new PCR ribotypes from the hypervirulent *Clostridium difficile* 027 lineage. *J Med Microbiol* 2012, 61(Pt 1):49-56.
2. Bartlett J G, Moon N, Chang T W, Taylor N, Onderdonk A B: Role of *Clostridium difficile* in antibiotic-associated pseudomembranous colitis. *Gastroenterology* 1978, 75(5):778-782.
3. Kato H, Kita H, Karasawa T, Maegawa T, Koino Y, Takakuwa H, Saikai T, Kobayashi K, Yamagishi T, Nakamura S: Colonisation and transmission of *Clostridium difficile* in healthy individuals examined by PCR ribotyping and pulsed-field gel electrophoresis. *J Med Microbiol* 2001, 50(8):720-727.
4. Rupnik M, Wilcox M H, Gerding D N: *Clostridium difficile* infection: new developments in epidemiology and pathogenesis. *Nat Rev Microbiol* 2009, 7(7):526-536.
5. Bartlett J G: *Clostridium difficile*-associated Enteric Disease. *Curr Infect Dis Rep* 2002, 4(6):477-483.
6. Kelly C P: Can we identify patients at high risk of recurrent *Clostridium difficile* infection? *Clin Microbiol Infect* 2012, 18 Suppl 6:21-27.
7. Deneve C, Janoir C, Poilane I, Fantinato C, Collignon A: New trends in *Clostridium difficile* virulence and pathogenesis. *Int J Antimicrob Agents* 2009, 33 Suppl 1:S24-28.
8. Kelly C P, Kyne L: The host immune response to *Clostridium difficile*. *J Med Microbiol* 2011, 60(Pt 8):1070-1079.
9. Kyne L, Warny M, Qamar A, Kelly C P: Association between antibody response to toxin A and protection against recurrent *Clostridium difficile* diarrhoea. *Lancet* 2001, 357(9251):189-193.
10. Bidet P, Lalande V, Salauze B, Burghoffer B, Avesani V, Delmee M, Rossier A, Barbut F, Petit J C: Comparison of PCR-ribotyping, arbitrarily primed PCR, and pulsed-field gel electrophoresis for typing *Clostridium difficile*. *J Clin Microbiol* 2000, 38(7):2484-2487.
11. Pechine S, Janoir C, Collignon A: Variability of *Clostridium difficile* surface proteins and specific serum antibody response in patients with *Clostridium difficile*-associated disease. *J Clin Microbiol* 2005, 43(10):5018-5025.
12. Tasteyre A, Karjalainen T, Avesani V, Delmee M, Collignon A, Bourlioux P, Barc M C: Molecular characterization of fliD gene encoding flagellar cap and its expression among *Clostridium difficile* isolates from different serogroups. *J Clin Microbiol* 2001, 39(3):1178-1183.
13. Waligora A J, Hennequin C, Mullany P, Bourlioux P, Collignon A, Karjalainen T: Characterization of a cell surface protein of *Clostridium difficile* with adhesive properties. *Infect Immun* 2001, 69(4):2144-2153.
14. Selby C: Interference in immunoassay. *Ann Clin Biochem* 1999, 36 (Pt 6):704-721.
15. Rousseau C, Poilane I, De Pontual L, Maherault A C, Le Monnier A, Collignon A: *Clostridium difficile* carriage in healthy infants in the community: a potential reservoir for pathogenic strains. *Clin Infect Dis* 2012, 55(9):1209-1215.
16. Lyras D, O'Connor J R, Howarth P M, Sambol S P, Carter G P, Phumoonna T, Poon R, Adams V, Vedantam G, Johnson S et al: Toxin B is essential for virulence of *Clostridium difficile*. *Nature* 2009, 458(7242):1176-1179.
17. Viscidi R, Laughon B E, Yolken R, Bo-Linn P, Moench T, Ryder R W, Bartlett J G: Serum antibody response to toxins A and B of *Clostridium difficile*. *J Infect Dis* 1983, 148(1):93-100.
18. Quinello C, Quintilio W, Carneiro-Sampaio M, Palmeira P: Passive acquisition of protective antibodies reactive with *Bordetella pertussis* in newborns via placental transfer and breast-feeding. *Scand J Immunol* 2010, 72(1):66-73.
19. Al-Jumaili I J, Shibley M, Lishman A H, Record C O: Incidence and origin of *Clostridium difficile* in neonates. *J Clin Microbiol* 1984, 19(1):77-78.
20. Kelly C P, Pothoulakis C, LaMont J T. *Clostridium difficile* colitis. N Engl J Med. 1994 Jan. 27; 330(4):257-62. Review.
21. Fekety R. Guidelines for the diagnosis and management of *Clostridium difficile*-associated diarrhea and colitis. American College of Gastroenterology, Practice Parameters Committee. Am J Gastroenterol. 1997 May; 92(5): 739-50. Review.
22. Wilcox M H. Treatment of *Clostridium difficile* infection. J Antimicrob Chemother. 1998 May; 41 Suppl C:41-6. Review.
23. McFarland L V, Surawicz C M, Rubin M, Fekety R, Elmer G W, Greenberg R N. Recurrent *Clostridium difficile* disease: epidemiology and clinical characteristics. Infect Control Hosp Epidemiol. 1999 January; 20(1):43-50.
24. Fekety R, McFarland L V, Surawicz C M, Greenberg R N, Elmer G W, Mulligan M E. Recurrent *Clostridium difficile* diarrhea: characteristics of and risk factors for patients enrolled in a prospective, randomized, double-blinded trial. Clin Infect Dis. 1997 March; 24(3):324-33.
25. Olson M M, Shanholtzer C J, Lee J T Jr, Gerding D N. Ten years of prospective *Clostridium difficile*-associated disease surveillance and treatment at the Minneapolis V A Medical Center, 1982-1991. Infect Control Hosp Epidemiol. 1994 June; 15(6):371-81.
26. Do A N, Fridkin S K, Yechouron A, Banerjee S N, Killgore G E, Bourgault A M, Jolivet M, Jarvis W R. Risk factors for early recurrent *Clostridium difficile*-associated diarrhea. Clin Infect Dis. 1998 April; 26(4):954-9.
27. Nair S, Yadav D, Corpuz M, Pitchumoni C S. *Clostridium difficile* colitis: factors influencing treatment failure and relapse—a prospective evaluation. Am J Gastroenterol. 1998 October; 93(10):1873-6.

The invention claimed is:

1. An in vitro method comprising:
   a) providing a sample from a human subject diagnosed with *Clostridium difficile*-Associated Disease (CDAD) and at risk of developing a recurrent CDAD or severe form of CDAD;
   b) quantitating in the sample IgG antibodies specifically binding the *C. difficile* toxin antigen TcdA, IgG antibodies specifically binding the *C. difficile* toxin antigen TcdB, IgG antibodies specifically binding the *C. difficile* antigen FliD, and IgM antibodies specifically binding the *C. difficile* antigen FliD; and
   c) administering to the human subject a treatment or an immunogenic composition against *C. difficile* infection when at least 0.38 µg/mL of IgG antibodies specifically binding the *C. difficile* toxin antigen TcdA, at least 1.56 µg/mL IgG antibodies specifically binding the *C. difficile* toxin antigen TcdB, at least 1.86 µg/mL IgG antibodies specifically binding the *C. difficile* antigen FliD, and at least 0.65 µg/mL IgM antibodies specifically binding the *C. difficile* antigen FliD, are not quantitated in the sample; and
   not administering to the human subject a treatment or an immunogenic composition against *C. difficile* infection when at least 0.38 µg/mL of IgG antibodies specifically binding the *C. difficile* toxin antigen TcdA, at least 1.56 µg/mL IgG antibodies specifically binding the *C. difficile* toxin antigen TcdB, at least 1.86 µg/mL IgG antibodies specifically binding the *C. difficile* antigen FliD, and at least 0.65 µg/mL IgM antibodies specifically binding the *C. difficile* antigen FliD, are quantitated in the sample.

2. The method of claim 1, further comprising a step of isolation and identification of a bacterial strain of *C. difficile*.

3. The method of claim 1, further comprising quantifying IgA antibodies in the sample.

4. The method of claim 1, wherein the sample is selected from the group consisting of: blood, cordblood, lactoserum, saliva and feces.

5. The method of claim 1, wherein at least 0.38 µg/mL of IgG antibodies specifically binding the *C. difficile* toxin antigen TcdA, at least 1.56 µg/mL IgG antibodies specifically binding the *C. difficile* toxin antigen TcdB, at least 1.86 µg/mL IgG antibodies specifically binding the *C. difficile* antigen FliD, and at least 0.65 µg/mL IgM antibodies specifically binding the *C. difficile* antigen FliD, are not quantitated in the sample; and
   wherein a treatment or an immunogenic composition against *C. difficile* infection is administered to the human subject.

6. The method of claim 1, wherein at least 0.38 µg/mL of IgG antibodies specifically binding the *C. difficile* toxin antigen TcdA, at least 1.56 µg/mL IgG antibodies specifically binding the *C. difficile* toxin antigen TcdB, at least 1.86 µg/mL IgG antibodies specifically binding the *C. difficile* antigen FliD, and at least 0.65 µg/mL IgM antibodies specifically binding the *C. difficile* antigen FliD, are quantitated in the sample; and
   wherein a treatment or an immunogenic composition against *C. difficile* infection is not administered to the human subject.

* * * * *